US010400290B2

(12) United States Patent
Parr et al.

(10) Patent No.: US 10,400,290 B2
(45) Date of Patent: Sep. 3, 2019

(54) MITOCHONDRIAL DNA DELETION BETWEEN ABOUT RESIDUES 12317-16254 FOR USE IN THE DETECTION OF CANCER

(71) Applicant: MDNA Life Sciences, Inc., West Palm Beach, FL (US)

(72) Inventors: Ryan Parr, Thunder Bay (CA); Jennifer Creed, Broomfield, CO (US); Kerry Robinson, Thunder Bay (CA); Andrea Maggrah, Thunder Bay (CA); Katrina Maki, Porcupine (CA); Gabriel Dakubo, Thunder Bay (CA); Brian Reguly, Thunder Bay (CA); Andrew Harbottle, Tyne and Wear (GB); Jude Alexander, Petawawa (CA)

(73) Assignee: MDNA Life Sciences, Inc., West Palm Beach, FL (US)

( * ) Notice: Subject to any disclaimer, the term of this patent is extended or adjusted under 35 U.S.C. 154(b) by 0 days.

(21) Appl. No.: 15/947,192

(22) Filed: Apr. 6, 2018

(65) Prior Publication Data
US 2018/0230549 A1    Aug. 16, 2018

Related U.S. Application Data

(63) Continuation of application No. 15/188,604, filed on Jun. 21, 2016, now abandoned, which is a continuation of application No. 14/489,119, filed on Sep. 17, 2014, now abandoned, which is a continuation of application No. 13/745,204, filed on Jan. 18, 2013, now abandoned, which is a continuation of application No. 12/742,032, filed as application No. PCT/CA2008/001956 on Nov. 10, 2008, now abandoned.

(60) Provisional application No. 61/002,637, filed on Nov. 9, 2007.

(51) Int. Cl.
C12Q 1/68        (2018.01)
C12Q 1/6886      (2018.01)

(52) U.S. Cl.
CPC ..... *C12Q 1/6886* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,800,992 A | 9/1998 | Fodor et al. |
| 6,582,908 B2 | 6/2003 | Fodor et al. |
| 2005/0026167 A1 | 2/2005 | Birch-Machin et al. |

FOREIGN PATENT DOCUMENTS

| | | |
|---|---|---|
| EP | 0849364 A1 | 6/1998 |
| WO | 2002/101086 A2 | 12/2002 |
| WO | 2005/056573 A1 | 6/2005 |
| WO | 2006/111029 A1 | 10/2006 |
| WO | 2009/039601 A1 | 4/2009 |

OTHER PUBLICATIONS

Birch-Machin et al., "Late-onset optic atrophy, ataxia, and myopathy associated with a mutation of a complex II gene," American Neurological Association, 48: 330-335 (2000).
Birch-Machin, "Mitochondria and skin disease," Clinical and Experimental Dermatology, 25: 141-146 (2000).
Brown et al., "Clustering of Caucasian Leber hereditary optic neuropathy patients containing the 11778 or 14484 mutations on an mtDNA lineage," American Society of Human Genetics, 60: 381-387 (1997).
Bogliolo et al., "Detection of the '4977 bp' mitochondrial DNA deletion in human atherosclerotic lesions," Mutagenesis, 14: 77-82 (1999).
Chinnery et al., "Mitochondrial DNA and disease," Molecular Medicine, 354: 17-21 (1999).
Huoponen, "Leber hereditary optic neuropathy: clinical and molecular genetic findings," Neurogenetics, 3: 119-125 (2001).
Hayward et al., "Genetic and epigenetic influences in prostatic carcinogenesis," International Journal of Oncology, 13: 35-47 (1998).
Huang et al., "Prostate Cancer Expression Profiling by cDNA Sequencing Analysis," Genomics, 59: 178-186 (1999).
Konishi et al., "Genetic changes in prostate cancer," Pathology International, 47: 735-747 (1997).
Landis et al., "Cancer Statistics," Cancer Journal for Clinicians, 49: 8-31 (1999).
Lee et al., "Aging- and smoking-associated alterations in the relative content of mitochondrial DNA in human lung," FEBS Letters, 441: 292-296 (1998).
Naviaux, The spectrum of Mitochondrial Disease, A Primary Care Physician's Guide, 3-10, (1997).
Parrella et al., "Detection of Mitochondrial DNA Mutations in Primary Breast Cancer and Fine-Needle Aspirates," Cancer Research, 61: 7623-7326 (2001).
Polyak et al., "Somatic mutations of the mitochondrial genome in human colorectal tumours," Nature Genetics, 20: 291-293 (1998).
Seidman et al., "Mitochondrial DNA Deletions Associated with Aging and Presbyacusis," Arch Otolaryngol Head Neck Surg, 123: 1039-1045 (1997).
Sherratt et al., "Mitochondrial DNA defects: a widening clinical spectrum of disorders," Clinical Science, 92: 225-235 (1997).
Shoffner et al., "Mitochondiral DNA variants observed in Alzheimer disease and Parkinson disease patients," Genomics, 17: 171-184 (1993).

(Continued)

*Primary Examiner* — Carla J Myers
(74) *Attorney, Agent, or Firm* — Morgan, Lewis & Bockius LLP

(57) ABSTRACT

The present invention relates to methods for predicting, diagnosing and monitoring cancer. The methods comprise obtaining biological samples, extracting mitochondrial DNA (mtDNA) from the samples, quantifying mitochondrial DNA mutation in the sample and comparing the level of mtDNA mutation with a reference value. The methods of the invention may also be effective in screening for new therapeutic agents and treatment regimes, and may also be useful for monitoring the response of a subject to a preventative or therapeutic treatment.

21 Claims, 6 Drawing Sheets

Specification includes a Sequence Listing.

(56) References Cited

OTHER PUBLICATIONS

Taniike et al., "Mitochondiral tRNAIle mutation in fatal cardiomyopathy," Biochemical and Biophysical Research Communications, 186: 47-53 (1992).
Valnot et al., "A mitochondrial cytochrome b mutation but no mutations of nuclearly encoded subunits in ubiquinol cytochrome c reductase (complex III) deficiency," Hum Genet, 104: 460-466 (1999).
von Wurmb et al., "Demonstration of the 4977 bp deletion in human mitochondrial DNA from intravital and postmortem blood," Mutation Research, 422: 247-254 (1998).
Wallace et al., "Mitochondrial DNA mutation associated with Leber's hereditary optic neuropathy," American Association for the Advancement of Science, 1427-1429 (1998).
Wei, "Mitochondiral DNA mutations and oxidative damage in aging and diseases: An emerging paradigm of gerontology and medicine," Proceedings of the National Science Council, ROC, 22, 55-67, (1998).
Woodwell, National ambulatory medical care survey: 1997 summary, Advance data from vital and health statistics, No. 305, (1999).
Yeh et al., Somatic mitochondrial DNA (mtDNA) mutations in papillary thyroid carcinomas and differential mtDNA sequence variants in cases with thyroid tumours, Oncogene, 19: 2060-2066 (2000).
Zhang et al., "Multiple mitochondrial DNA deletions in an elderly human individual," FEBS, 297: 34-38 (1992).
Zhang et al., "Occurrence of a particular base substitution (3243 A to G) in mitochondiral DNA of tissues of ageing humans," Biochemical and Biophysical Research Communications, 195: 1104-1110 (1993).
Krishnan et al., "The use of a 3895 bp mitochondiral DNA deletion as a marker for sunlight exposure in human skin," Society for Investigative Dermatology, 123: 1020-1024 (2004).
Chatterjee, Mitochondiral DNA mutations in human cancer, Oncogene, 25: 4663-4674 (2006).
Zhu, Large-scale mitochondrial DNA deletion mutations and nuclear genome instability in human breast cancer, Cancer Detection and Prevention, 28: 119-126 (2004).
International Search Report from PCT/CA2008/001956 dated Apr. 2, 2009.
Tan et al., "Comprehensive Scanning of Somatic Mitochondrial DNA Mutations in Breast Cancer," Cancer Research, 62: 972-976 (2002).
Chabi et al., "Quantification of Mitochondrial DNA Deletion, Depletion, and Overreplication: Application to Diagnosis," Clinical Chemistry, 49: 1309-1317 (2003).
Maximo et al., "Mitochondrial DNA Somatic Mutations (Point Mutations and Large Deletions) and Mitochondrial DNA Variants in Human Thyroid Pathology," The American Journal of Pathology, 160: 1857-1865 (2002).
European Search Report issued in related European Patent Application No. 080846547 dated Jul. 13, 2012.
Marin-Garcia et al., "Specific mitochondrial DNA deletions in idiopathic dilated cariomyopathy," Cardiovascular Research, 31: 306-313 (1996).
Hirschhorn et al. "A comprehensive review of genetic association studies," Genetics in Medicine, 4: 46-61 (2002).
Lucentini, "Gene Association Studies Typically Wrong," The Scientists, 18: 20 (2004).
Guo et al., "Mitochondrial DNA deletions in Mice in Men: substantia nigra is much less affected in the mouse," Biochem Biophys Acta 1797: 1159-1162 (2010).
Schlick et al., "Sequence analysis of the complete mitochondrial DNA in 10 commonly used inbred rat strains," Am J Physiol. 291: C1183-C1192 (2006).
Aral et al. "Mitochondrial DNA common deletion is not associated with thyroid, breast and colorectal tumors in Turkish patients," Genetics and Molecular Biology, 33: 1-4 (2010).
Fang et al. "Cancer type-specific modulation of mitochondrial haplogroups in breast, colorectal and thyroid cancer," BMC Cancer, 10: 421 (2010).
Durham et al., "Mitochondrial DNA damage in non-melanoma skin cancer," British Journal of Cancer 88: 90-95 (2003).
Ye et al., "Quantitative analysis of mitochondrial DNA 4977-bp deletion in sporadic breast cancer and benign breast diseases," Breast Cancer Research and Treatment, 108: 427-434 (2008).
Cormier-Daire et al., "Mitochondrial DNA rearrangements with onset as chronic diarrhea with villous atrophy," The Journal of Pediatrics, 124: 63-70 (1994).
National Center for Biotechnology Information (NCBI), National Library of Medicine (Bethesda, MD, USA), GenBank Accession No. NC_0129920 Jul. 8, 2009.
National Center for Biotechnology Information (NCBI), National Library of Medicine (Bethesda, MD, USA), GenBank Accession No. D38112.1 Oct. 11, 2008.
National Center for Biotechnology Information (NCBI), National Library of Medicine (Bethesda, MD, USA), GenBank Accession No. AB055387 Jul. 14, 2007.
Tengan et al., "Detection and Analysis of Mitochondrial DNA Deletions by Whole Genome PCR," Biochemical and Molecular Medicine, 58: 130-134 (1996).
Extended European Search Report issued in corresponding European Patent Application No. 18160726.8 dated Aug. 24, 2018.

SEQUENCE LISTING

```
<160> NUMBER OF SEQ ID NOS: 9

<210> SEQ ID NO 1
<211> LENGTH: 3926
<212> TYPE: DNA
<213> ORGANISM: Homo sapiens

<400> SEQUENCE: 1
taaaagtaat aaccatgcac actactataa ccaccctaac cctgacttcc ctaattcccc      60
ccatccttac caccctcgtt aaccctaaca aaaaaaactc ataccccat tatgtaaaat      120 ccattgtcgc atccaccttt attatcagtc tcttccccac aacaatattc atgtgcctag    180
accaagaagt tattatctcg aactgacact gagccacaac ccaaacaacc cagctctccc    240
taagcttcaa actagactac ttctccataa tattcatccc tgtagcattg ttcgttacat    300
ggtccatcat agaattctca ctgtgatata taaactcaga cccaaacatt aatcagttct    360
tcaaatatct actcatcttc ctaattacca tactaatctt agttaccgct aacaacctat    420
tccaactgtt catcggctga gagggcgtag gaattatatc cttcttgctc atcagttgat    480
gatacgcccg agcagatgcc aacacagcag ccattcaagc aatcctatac aaccgtatcg    540
gcgatatcgg tttcatcctc gccttagcat gatttatcct acactccaac tcatgagacc    600
cacaacaaat agcccttcta aacgctaatc caagcctcac cccactacta ggcctcctcc    660
```

```
tagcagcagc aggcaaatca gcccaattag gtctccaccc ctgactcccc tcagccatag    720
aaggccccac cccagtctca gccctactcc actcaagcac tatagttgta gcaggaatct    780
tcttactcat ccgcttccac cccctagcag aaaatagccc actaatccaa actctaacac    840
tatgctaggc gctatcacc actctgttcg cagcagtctg cgcccttaca caaaatgaca     900
tcaaaaaaat cgtagccttc tccacttcaa gtcaactagg actcataata gttacaatcg    960
gcatcaacca accacaccta gcattcctgc acatctgtac ccacgccttc ttcaaagcca   1020
tactatttat gtgctccggg tccatcatcc acaaccttaa caatgaacaa gatattcgaa   1080
aaataggagg actactcaaa accataccte tcacttcaac ctccctcacc attggcagcc   1140
tagcattagc aggaatacct ttcctcacag gtttctactc caaagaccac atcatcgaaa   1200
ccgcaaacat atcatacaca aacgcctgag ccctatctat tactctcatc gctacctccc   1260
tgacaagcgc ctatagcact cgaataattc ttctcaccct aacaggtcaa cctcgcttcc   1320
ccacccttac taacattaac gaaaataacc ccaccctact aaaccccatt aaacgcctgg   1380
cagccggaag cctattcgca ggatttctca ttactaacaa catttccccc gcatcccct   1440 tccaaacaac aatcccccte tacctaaaac tcacagccct cgctgtcact ttcctaggac   1500
ttctaacagc cctagacctc aactacctaa ccaacaaact taaaataaaa tccccactat   1560
gcacatttta tttctccaac atactcggat tctaccctag catcacacac cgcacaatcc   1620
cctatctagg ccttcttacg agccaaaacc tgccccctact cctcctagac ctaacctgac   1680
tagaaaagct attacctaaa acaatttcac agcaccaaat ctccacctcc atcatcacct   1740
caacccaaaa aggcataatt aaactttact tcctctcttt cttcttccca ctcatcctaa   1800
ccctactcct aatcacataa cctattcccc cgagcaatct caattacaat atatacacca   1860
acaaacaatg ttcaaccagt aactactact aatcaacgcc cataatcata caaagccccc   1920
gcaccaatag gatcctcccg aatcaaccct gaccctctc cttcataaat tattcagctt   1980
cctacactat taaagtttac cacaaccacc accccatcat actctttcac ccacagcacc   2040
aatcctacct ccatcgctaa ccccactaaa acactcacca agacctcaac ccctgacccc   2100
catgcctcag gatactcctc aatagccatc gctgtagtat atccaaagac aaccatcatt   2160 cccccctaaat aaattaaaaa aactattaaa cccatataac ctcccccaaa attcagaata   2220
ataacacacc cgaccacacc gctaacaatc aatactaaac cccccataaat aggagaaggc   2280 ttagaagaaa accccacaaa ccccattact aaacccacac tcaacagaaa caaagcatac   2340
atcattattc tcgcacggac tacaaccacg accaatgata tgaaaaacca tcgttgtatt   2400
tcaactacaa gaacaccaat gaccccaata cgcaaaacta accccctaat aaaattaatt   2460
aaccactcat tcatcgacct ccccacccca tccaacatct ccgcatgatg aaacttcggc   2520
tcactccttg gcgcctgcct gatcctccaa atcaccacag gactattcct agccatgcac   2580
tactcaccag acgcctcaac cgcctttta tcaatcgccc acatcactcg agacgtaaat   2640
tatggctgaa tcatccgcta ccttcacgcc aatggcgcct caatattctt tatctgcctc   2700
ttcctacaca tcgggcgagg cctatattac ggatcatttc tctactcaga aacctgaaac   2760
atcggcatta tcctcctgct tgcaactata gcaacagcct tcataggcta tgtcctcccg   2820
tgaggccaaa tatcattctg aggggccaca gtaattacaa acttactatc cgccatccca   2880
tacattggga cagacctagt tcaatgaatc tgaggaggct actcagtaga cagtcccacc   2940
ctcacacgat tctttacctt tcacttcatc ttgcccttca ttattgcagc cctagcaaca   3000
ctccacctcc tattcttgca cgaaacggga tcaaacaacc ccctaggaat cacctcccat   3060
```

| | |
|---|---|
| tccgataaaa tcaccttcca cccttactac acaatcaaag acgccctcgg cttacttctc | 3120 |
| ttccttctct ccttaatgac attaacacta ttctcaccag acctcctagg cgacccagac | 3180 |
| aattataccc tagccaaccc cttaaacacc cctccccaca tcaagcccga atgatatttc | 3240 |
| ctattcgcct acacaattct ccgatccgtc cctaacaaac taggaggcgt ccttgcccta | 3300 |
| ttactatcca tcctcatcct agcaataatc cccatcctcc atatatccaa acaacaaagc | 3360 |
| ataatatttc gcccactaag ccaatcactt tattgactcc tagccgcaga cctcctcatt | 3420 |
| ctaacctgaa tcggaggaca accagtaagc tacccttttta ccatcattgg acaagtagca | 3480 |
| tccgtactat acttcacaac aatcctaatc ctaataccaa ctatctccct aattgaaaac | 3540 |
| aaaatactca aatgggcctg tccttgtagt ataaactaat acaccagtct tgtaaaccgg | 3600 |
| agatgaaaac cttttttccaa ggacaaatca gagaaaaagt ctttaactcc accattagca | 3660 |
| cccaaagcta agattctaat ttaaactatt ctctgttctt tcatggggaa gcagatttgg | 3720 |
| gtaccaccca gtattgact cacccatcaa caaccgctat gtatttcgta cattactgcc | 3780 |
| agccaccatg aatattgtac ggtaccataa atacttgacc cctgtagta cataaaaacc | 3840 |
| caatccacat caaaaccccc tccccatgct tacaagcaag tacagcaatc aaccctcaac | 3900 |
| tatcacacat caactgcaac tccaaa | 3926 |

<210> SEQ ID NO 2
<211> LENGTH: 3926
<212> TYPE: DNA
<213> ORGANISM: Homo sapiens

<400> SEQUENCE: 2

| | |
|---|---|
| tgcaactcca aataaaagta ataaccatgc acactactat aaccacccta accctgactt | 60 |
| ccctaattcc ccccatcctt accaccctcg ttaaccctaa caaaaaaaac tcatacccccc | 120 |
| attatgtaaa atccattgtc gcatccacct ttattatcag tctcttcccc acaacaatat | 180 |
| tcatgtgcct agaccaagaa gttattatct cgaactgaca ctgagccaca acccaaacaa | 240 |
| cccagctctc cctaagcttc aaactagact acttctccat aatattcatc cctgtagcat | 300 |
| tgttcgttac atggtccatc atagaattct cactgtgata tataaactca gacccaaaca | 360 |
| ttaatcagtt cttcaaatat ctactcatct tcctaattac catactaatc ttagttaccg | 420 |
| ctaacaacct attccaactg ttcatcggct gagagggcgt aggaattata tccttcttgc | 480 |
| tcatcagttg atgatacgcc cgagcagatg ccaacacagc agccattcaa gcaatcctat | 540 |
| acaaccgtat cggcgatatc ggtttcatcc tcgccttagc atgatttatc ctacactcca | 600 |
| actcatgaga cccacaacaa atagcccttc taaacgctaa tccaagcctc accccactac | 660 |
| taggcctcct cctagcagca gcaggcaaat cagcccaatt aggtctccac ccctgactcc | 720 |
| cctcagccat agaaggcccc accccagtct cagccctact ccactcaagc actatagttg | 780 |
| tagcaggaat cttcttactc atccgcttcc accccctagc agaaaatagc ccactaatcc | 840 |
| aaactctaac actatgctta ggcgctatca ccactctgtt cgcagcagtc tgcgccctta | 900 |
| cacaaaatga catcaaaaaa atcgtagcct tctccacttc aagtcaacta ggactcataa | 960 |
| tagttacaat cggcatcaac caaccacacc tagcattcct gcacatctgt acccacgcct | 1020 |
| tcttcaaagc catactattt atgtgctccg ggtccatcat ccacaacctt aacaatgaac | 1080 |
| aagatattcg aaaaatagga ggactactca aaaccatacc tctcacttca acctccctca | 1140 |
| ccattggcag cctagcatta gcaggaatac ctttcctcac aggtttctac tccaaagacc | 1200 |

```
acatcatcga aaccgcaaac atatcataca caaacgcctg agccctatct attactctca    1260
tcgctacctc cctgacaagc gcctatagca ctcgaataat tcttctcacc ctaacaggtc    1320
aacctcgctt ccccacccct actaacatta acgaaaataa ccccacccta ctaaacccca    1380
ttaaacgcct ggcagccgga agcctattcg caggatttct cattactaac aacatttccc    1440
ccgcatcccc cttccaaaca caatccccc tctacctaaa actcacagcc ctcgctgtca    1500
ctttcctagg acttctaaca gccctagacc tcaactacct aaccaacaaa cttaaaataa    1560
aatccccact atgcacattt tatttctcca acatactcgg attctaccct agcatcacac    1620
accgcacaat cccctatcta ggccttctta cgagccaaaa cctgccccta ctcctcctag    1680
acctaacctg actagaaaag ctattaccta aaacaatttc acagcaccaa atctccacct    1740
ccatcatcac ctcaacccaa aaaggcataa ttaaacttta cttcctctct ttcttcttcc    1800
cactcatcct aaccctactc ctaatcacat aacctattcc cccgagcaat ctcaattaca    1860
atatatacac caacaaacaa tgttcaacca gtaactacta ctaatcaacg cccataatca    1920
tacaaagccc ccgcaccaat aggatcctcc cgaatcaacc ctgaccccct ccttcataa    1980 attattcagc ttcctacact attaaagttt accacaacca ccaccccatc atactctttc    2040
acccacagca ccaatcctac ctccatcgct aaccccacta aaacactcac caagacctca    2100 accctgacc cccatgcctc aggatactcc tcaatagcca tcgctgtagt atatccaaag    2160
acaaccatca ttccccctaa ataaattaaa aaaactatta aacccatata acctccccca    2220
aaattcagaa taataacaca cccgaccaca ccgctaacaa tcaatactaa accccataa    2280 ataggagaag gcttagaaga aaccccccaca aaccccatta ctaaacccac actcaacaga    2340
aacaaagcat acatcattat tctcgcacgg actacaacca cgaccaatga tatgaaaaac    2400
catcgttgta tttcaactac aagaacacca atgaccccaa tacgcaaaac taaccccta    2460 ataaaattaa ttaaccactc attcatcgac ctccccaccc catccaacat ctccgcatga    2520
tgaaacttcg gctcactcct tggcgcctgc ctgatcctcc aaatcaccac aggactattc    2580
ctagccatgc actactcacc agacgcctca accgcttttt catcaatcgc ccacatcact    2640
cgagacgtaa attatggctg aatcatccgc taccttcacg ccaatggcgc ctcaatattc    2700
tttatctgcc tcttcctaca catcgggcga ggcctatatt acggatcatt tctctactca    2760
gaaacctgaa acatcggcat tatcctcctg cttgcaacta tagcaacagc cttcataggc    2820
tatgtcctcc cgtgaggcca aatatcattc tgaggggcca cagtaattac aaacttacta    2880
tccgccatcc catacattgg gacagaccta gttcaatgaa tctgaggagg ctactcagta    2940
gacagtccca ccctcacacg attctttacc tttcacttca tcttgccctt cattattgca    3000
gccctagcaa cactccacct cctattcttg cacgaaacgg gatcaaacaa ccccctagga    3060
atcacctccc attccgataa aatcaccttc caccttact acacaatcaa agacgccctc    3120
ggcttacttc tcttccttct ctccttaatg acattaacac tattctcacc agacctccta    3180
ggcgacccag acaattatac cctagccaac cccttaaaca cccctcccca catcaagccc    3240
gaatgatatt tcctattcgc ctacacaatt ctccgatccg tccctaacaa actaggaggc    3300
gtccttgccc tattactatc catcctcatc ctagcaataa tccccatcct ccatatatcc    3360
aaacaacaaa gcataatatt tcgcccacta agccaatcac tttattgact cctagccgca    3420
gacctcctca ttctaacctg aatcggagga caaccagtaa gctaccttt taccatcatt    3480 ggacaagtag catccgtact atacttcaca acaatcctaa tcctaatacc aactatctcc    3540
ctaattgaaa acaaaatact caaatgggcc tgtccttgta gtataaacta atacaccagt    3600
```

```
cttgtaaacc ggagatgaaa accttttcc aaggacaaat cagagaaaaa gtctttaact    3660
ccaccattag cacccaaagc taagattcta atttaaacta ttctctgttc tttcatgggg    3720
aagcagattt gggtaccacc caagtattga ctcacccatc aacaaccgct atgtatttcg    3780
tacattactg ccagccacca tgaatattgt acggtaccat aaatacttga ccacctgtag    3840
tacataaaaa cccaatccac atcaaaaccc cctccccatg cttacaagca agtacagcaa    3900
tcaaccctca actatcacac atcaac                                        3926
```

```
<210> SEQ ID NO 3
<211> LENGTH: 16569
<212> TYPE: DNA
<213> ORGANISM: Homo sapiens
<220> FEATURE:
<221> NAME/KEY: misc_feature
<222> LOCATION: (3107)..(3107)
<223> OTHER INFORMATION: n is a, c, g, or t

<400> SEQUENCE: 3
```

```
gatcacaggt ctatcaccct attaaccact cacgggagct ctccatgcat ttggtatttt      60
cgtctggggg gtatgcacgc gatagcattg cgagacgctg gagccggagc accctatgtc     120
gcagtatctg tctttgattc ctgcctcatc ctattattta tcgcacctac gttcaatatt     180
acaggcgaac atacttacta agtgtgtta attaattaat gcttgtagga cataataata     240
acaattgaat gtctgcacag ccactttcca cacagacatc ataacaaaaa atttccacca     300
aaccccccct cccccgcttc tggccacagc acttaaacac atctctgcca aaccccaaaa     360
acaaagaacc ctaacaccag cctaaccaga tttcaaattt tatcttttgg cggtatgcac     420
ttttaacagt cacccccaa ctaacacatt attttcccct cccactccca tactactaat     480
ctcatcaata caaccccgc ccatcctacc cagcacacac acaccgctgc taaccccata     540
ccccgaacca accaaacccc aaagacaccc ccacagtttt atgtagctta cctcctcaaa     600
gcaatacact gaaaatgttt agacgggctc acatcaccc ataaacaaat aggtttggtc     660
ctagcctttc tattagctct tagtaagatt acacatgcaa gcatcccgt tccagtgagt     720 tcaccctcta aatcaccacg atcaaaagga acaagcatca agcacgcagc aatgcagctc     780
aaaacgctta gcctagccac ccccccacgg gaaacagcag tgattaacct ttagcaataa     840
acgaaagttt aactaagcta tactaacccc agggttggtc aatttcgtgc cagccaccgc     900
ggtcacacga ttaacccaag tcaatagaag ccggcgtaaa gagtgtttta gatcaccccc     960
tccccaataa agctaaaact cacctgagtt gtaaaaaact ccagttgaca caaaatagac    1020
tacgaaagtg gctttaacat atctgaacac acaatagcta agacccaaac tgggattaga    1080
taccccacta tgcttagccc taaacctcaa cagttaaatc aacaaaactg ctcgccagaa    1140
cactacgagc cacagcttaa aactcaaagg acctggcggt gcttcatatc cctctagagg    1200
agcctgttct gtaatcgata accccgatc aacctcacca cctcttgctc agcctatata    1260
ccgccatctt cagcaaaccc tgatgaaggc tacaaagtaa gcgcaagtac ccacgtaaag    1320
acgttaggtc aaggtgtagc ccatgaggtg gcaagaaatg ggctacattt tctaccccag    1380
aaaactacga tagcccttat gaaacttaag ggtcgaaggt ggatttagca gtaaactaag    1440
agtagagtgc ttagttgaac agggccctga agcgcgtaca caccgcccgt caccctcctc    1500
aagtatactt caaaggacat ttaactaaaa cccctacgca tttatataga ggagacaagt    1560
cgtaacatgg taagtgtact ggaaagtgca cttggacgaa ccagagtgta gcttaacaca    1620
```

```
aagcacccaa cttacactta ggagatttca acttaacttg accgctctga gctaaaccta    1680
gccccaaacc cactccacct tactaccaga caaccttagc caaaccattt acccaaataa    1740
agtataggcg atagaaattg aaacctggcg caatagatat agtaccgcaa gggaaagatg    1800
aaaaattata accaagcata atatagcaag gactaacccc tataccttct gcataatgaa    1860
ttaactagaa ataactttgc aaggagagcc aaagctaaga cccccgaaac cagacgagct    1920
acctaagaac agctaaaaga gcacacccgt ctatgtagca aaatagtggg aagatttata    1980
ggtagaggcg acaaacctac cgagcctggt gatagctggt tgtccaagat agaatcttag    2040
ttcaacttta aatttgccca cagaaccctc taaatcccct tgtaaattta actgttagtc    2100
caaagaggaa cagctctttg gacactagga aaaaccttg tagagagagt aaaaaattta     2160
acacccatag taggcctaaa agcagccacc aattaagaaa gcgttcaagc tcaacaccca    2220
ctacctaaaa aatcccaaac ataactga actcctcaca cccaattgga ccaatctatc      2280
accctataga agaactaatg ttagtataag taacatgaaa acattctcct ccgcataagc    2340
ctgcgtcaga ttaaaacact gaactgacaa ttaacagccc aatatctaca atcaaccaac    2400
aagtcattat taccctcact gtcaacccaa cacaggcatg ctcataagga aaggttaaaa    2460
aaagtaaaag gaactcggca aatcttaccc cgcctgttta ccaaaaacat cacctctagc    2520
atcaccagta ttagaggcac cgcctgccca gtgacacatg tttaacggcc gcggtaccct    2580
aaccgtgcaa aggtagcata atcacttgtt ccttaaatag ggacctgtat gaatggctcc    2640
acgagggttc agctgtctct tactttaac cagtgaaatt gacctgcccg tgaagaggcg      2700
ggcataacac agcaagacga gaagaccccta tggagcttta atttattaat gcaaacagta    2760
cctaacaaac ccacaggtcc taaactacca aacctgcatt aaaaatttcg gttggggcga    2820
cctcggagca gaacccaacc tccgagcagt acatgctaag acttcaccag tcaaagcgaa    2880
ctactatact caattgatcc aataacttga ccaacgaac aagttaccct agggataaca      2940
gcgcaatcct attctagagt ccatatcaac aataggtttt acgacctcga tgttggatca    3000
ggacatcccg atggtgcagc cgctattaaa ggttcgtttg ttcaacgatt aaagtcctac    3060
gtgatctgag ttcagaccgg agtaatccag gtcggtttct atctacnttc aaattcctcc    3120
ctgtacgaaa ggacaagaga aataaggcct acttcacaaa gcgccttccc ccgtaaatga    3180
tatcatctca acttagtatt atacccacac ccacccaaga acagggtttg ttaagatggc    3240
agagcccggt aatcgcataa aacttaaaac tttacagtca gaggttcaat tcctcttctt    3300
aacaacatac ccatggccaa cctcctactc ctcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc ctccccatac caaccccct ggtcaacctc      3600 aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
tgacccttgg ccataatatg atttatctcc acactagcag agaccaaccg aacccccttc    3900 gaccttgccag aaggggagtc cgaactagtc tcaggcttca acatcgaata cgccgcaggc    3960
cccttcgccc tattcttcat agccgaatac acaaacatta ttataataaa cacccctcacc   4020
```

```
actacaatct tcctaggaac aacatatgac gcactctccc ctgaactcta cacaacatat    4080
tttgtcacca agaccctact tctaacctcc ctgttcttat gaattcgaac agcataccccc   4140 cgattccgct acgaccaact catacacctc ctatgaaaaa acttcctacc actcacccta    4200
gcattactta tatgatatgt ctccataccc attacaatct ccagcattcc ccctcaaacc    4260
taagaaatat gtctgataaa agagttactt tgatagagta ataataggga gcttaaaccc    4320
ccttatttct aggactatga gaatcgaacc catccctgag aatccaaaat tctccgtgcc    4380
acctatcaca ccccatccta aagtaaggtc agctaaataa gctatcgggc ccataccccg    4440
aaaatgttgg ttatacccctt cccgtactaa ttaatcccct ggcccaaccc gtcatctact   4500
ctaccatctt tgcaggcaca ctcatcacag cgctaagctc gcactgattt tttacctgag    4560
taggcctaga aataaacatg ctagcttttta ttccagttct aaccaaaaaa ataaaccctc   4620
gttccacaga agctgccatc aagtatttcc tcacgcaagc aaccgcatcc ataatccttc    4680
taatagctat cctcttcaac aatatactct ccggacaatg aaccataacc aatactacca    4740
atcaatactc atcattaata atcataatag ctatagcaat aaaactagga atagccccct    4800
ttcacttctg agtcccagag gttacccaag gcacccctct gacatccggc ctgcttcttc    4860
tcacatgaca aaaactagcc cccatctcaa tcatatacca aatctctccc tcactaaacg    4920
taagccttct cctcactctc tcaatcttat ccatcatagc aggcagttga ggtggattaa    4980
accaaaccca gctacgcaaa atcttagcat actcctcaat tacccacata ggatgaataa    5040
tagcagttct accgtacaac cctaacataa ccattcttaa tttaactatt tatattatcc    5100
taactactac cgcattccta ctactcaact aaaactccag caccacgacc ctactactat    5160
ctcgcacctg aaacaagcta acatgactaa caccccttaat tccatccacc ctcctctccc   5220
taggaggcct gcccccgcta accggctttt tgcccaaatg ggccattatc gaagaattca    5280
caaaaaacaa tagcctcatc atccccacca tcatagccac catcaccctc cttaacctct    5340
acttctacct acgcctaatc tactccacct caatcacact actccccata tctaacaacg    5400
taaaaataaa atgacagttt gaacatacaa aacccacccc attcctcccc acactcatcg    5460
cccttaccac gctactccta cctatctccc cttttatact aataatctta tagaaattta    5520
ggttaaatac agaccaagag ccttcaaagc cctcagtaag ttgcaatact taatttctgt    5580
aacagctaag gactgcaaaa ccccactctg catcaactga acgcaaatca gccacttttaa   5640 ttaagctaag cccttactag accaatggga cttaaaccca caaacactta gttaacagct    5700
aagcacccta atcaactggc ttcaatctac ttctcccgcc gccgggaaaa aaggcgggag    5760
aagccccggc aggtttgaag ctgcttcttc gaatttgcaa ttcaatatga aaatcacctc    5820
ggagctggta aaaagaggcc taaccctgt ctttagattt acagtccaat gcttcactca     5880
gccattttac ctcaccccca ctgatgttcg ccgaccgttg actattctct acaaaccaca    5940
aagacattgg aacactatac ctattattcg gcgcatgagc tggagtccta ggcacagctc    6000
taagcctcct tattcgagcc gagctgggcc agccaggcaa ccttctaggt aacgaccaca    6060
tctacaacgt tatcgtcaca gcccatgcat ttgtaataat cttcttcata gtaatacccca   6120 tcataatcgg aggctttggc aactgactag ttcccctaat aatcggtgcc cccgatatgg    6180
cgtttccccg cataaacaac ataagcttct gactcttacc tccctctctc ctactcctgc    6240
tcgcatctgc tatagtggag gccggagcag gaacaggttg aacagtctac cctcccttag    6300
cagggaacta ctcccaccct ggagcctccg tagacctaac catcttctcc ttacacctag    6360
```

-continued

```
caggtgtctc ctctatctta ggggccatca atttcatcac acaattatc aatataaaac    6420
cccctgccat aacccaatac caaacgcccc tcttcgtctg atccgtccta atcacagcag    6480
tcctacttct cctatctctc ccagtcctag ctgctggcat cactatacta ctaacagacc    6540
gcaacctcaa caccaccttc ttcgaccccg ccggaggagg agaccccatt ctataccaac    6600
acctattctg attttttcggt caccctgaag tttatattct tatcctacca ggcttcggaa    6660
taatctccca tattgtaact tactactccg gaaaaaaaga accatttgga tacataggta    6720
tggtctgagc tatgatatca attggcttcc tagggtttat cgtgtgagca caccatatat    6780
ttacagtagg aatagacgta gacacacgag catatttcac ctccgctacc ataatcatcg    6840
ctatccccac cggcgtcaaa gtatttagct gactcgccac actccacgga agcaatatga    6900
aatgatctgc tgcagtgctc tgagccctag gattcatctt tcttttcacc gtaggtggcc    6960
tgactggcat tgtattagca aactcatcac tagacatcgt actacacgac acgtactacg    7020
ttgtagccca cttccactat gtcctatcaa taggagctgt atttgccatc ataggaggct    7080
tcattcactg atttcccccta ttctcaggct acaccctaga ccaaacctac gccaaaatcc    7140
atttcactat catattcatc ggcgtaaatc taactttctt cccacaacac tttctcggcc    7200
tatccggaat gccccgacgt tactcggact accccgatgc atacaccaca tgaaacatcc    7260
tatcatctgt aggctcattc atttctctaa cagcagtaat attaataatt ttcatgattt    7320
gagaagcctt cgcttcgaag cgaaaagtcc taatagtaga agaaccctcc ataaacctgg    7380
agtgactata tggatgcccc ccaccctacc acacattcga agaacccgta tacataaaat    7440
ctagacaaaa aaggaaggaa tcgaacccc caaagctggt ttcaagccaa ccccatggcc    7500
tccatgactt tttcaaaaag gtattagaaa aaccatttca taactttgtc aaagttaaat    7560
tataggctaa atcctatata tcttaatggc acatgcagcg caagtaggtc tacaagacgc    7620
tacttcccct atcatagaag agcttatcac ctttcatgat cacgccctca taatcatttt    7680
ccttatctgc ttcctagtcc tgtatgccct tttcctaaca ctcacaacaa aactaactaa    7740
tactaacatc tcagacgctc aggaaataga aaccgtctga actatcctgc ccgccatcat    7800
cctagtcctc atcgccctcc catccctacg catcctttac ataacagacg aggtcaacga    7860
tccctccctt accatcaaat caattggcca ccaatggtac tgaacctacg agtacaccga    7920
ctacggcgga ctaatcttca actcctacat acttccccca ttattcctag aaccaggcga    7980
cctgcgactc cttgacgttg acaatcgagt agtactcccg attgaagccc ccattcgtat    8040
aataattaca tcacaagacg tcttgcactc atgagctgtc cccacattag cttaaaaaac    8100
agatgcaatt cccggacgtc taaaccaaac cactttcacc gctacacgac cggggggtata    8160
ctacggtcaa tgctctgaaa tctgtgggagc aaaccacagt ttcatgccca tcgtcctaga    8220
attaattccc ctaaaaatct tgaaatagg gcccgtattt accctatagc accccctcta    8280
cccctctag agcccactgt aaagctaact tagcattaac ctttaagtt aaagattaag    8340
agaaccaaca cctctttaca gtgaaatgcc ccaactaaat actaccgtat ggcccaccat    8400
aattaccccc atactccttta cactattcct catcacccaa ctaaaaatat aaacacaaa    8460
ctaccaccta cctccctcac caaagcccat aaaaataaaa aattataaca aaccctgaga    8520
accaaaatga acgaaaatct gttcgcttca ttcattgccc ccacaatcct aggcctaccc    8580
gccgcagtac tgatcattct atttcccccct ctattgatcc ccacctccaa atatctcatc    8640
aacaaccgac taatcaccac ccaacaatga ctaatcaaac taacctcaaa acaaatgata    8700
accatacaca acactaaagg acgaacctga tctcttatac tagtatcctt aatcatttt    8760
```

```
attgccacaa ctaacctcct cggactcctg cctcactcat ttacaccaac cacccaacta   8820
tctataaacc tagccatggc catcccctta tgagcgggca cagtgattat aggctttcgc   8880
tctaagatta aaaatgccct agcccacttc ttaccacaag gcacacctac acccottatc   8940 cccatactag ttattatcga aaccatcagc ctactcattc aaccaatagc cctggccgta   9000
cgcctaaccg ctaacattac tgcaggccac ctactcatgc acctaattgg aagcgccacc   9060
ctagcaatat caaccattaa ccttccctct acacttatca tcttcacaat tctaattcta   9120
ctgactatcc tagaaatcgc tgtcgcctta atccaagcct acgttttcac acttctagta   9180
agcctctacc tgcacgacaa cacataatga cccaccaatc acatgcctat catatagtaa   9240
aacccagccc atgaccccta cagggggccc tctcagccct cctaatgacc tccggcctag   9300
ccatgtgatt tcacttccac tccataacgc tcctcatact aggcctacta accaacacac   9360
taaccatata ccaatgatgg cgcgatgtaa cacgagaaag cacataccaa ggccaccaca   9420
caccacctgt ccaaaaaggc cttcgatacg ggataatcct atttattacc tcagaagttt   9480
ttttcttcgc aggatttttc tgagcctttt accactccag cctagcccct acccccccaat   9540 taggagggca ctggcccca acaggcatca ccccgctaaa tcccctagaa gtcccactcc   9600
taaacacatc cgtattactc gcatcaggag tatcaatcac ctgagctcac catagtctaa   9660
tagaaaacaa ccgaaaccaa ataattcaag cactgcttat tacaattta ctgggtctct   9720 attttaccct cctacaagcc tcagagtact tcgagtctcc cttcaccatt tccgacggca   9780
tctacggctc aacattttttt gtagccacag gcttccacgg acttcacgtc attattggct   9840
caactttcct cactatctgc ttcatccgcc aactaatatt tcactttaca tccaaacatc   9900
actttggctt cgaagccgcc gcctgatact ggcattttgt agatgtggtt tgactatttc   9960
tgtatgtctc catctattga tgagggtctt actcttttag tataaatagt accgttaact  10020
tccaattaac tagttttgac aacattcaaa aagagtaat aaacttcgcc ttaattttaa  10080
taatcaacac cctcctagcc ttactactaa taattattac atttttgacta ccacaactca  10140 acggctacat agaaaaatcc accccttacg agtgcggctt cgaccctata tcccccgccc  10200
gcgtcccttt ctccataaaa ttcttcttag tagctattac cttcttatta tttgatctag  10260
aaattgccct ccttttaccc ctaccatgag ccctacaaac aactaacctg ccactaatag  10320
ttatgtcatc cctcttatta atcatcatcc tagccctaag tctggcctat gagtgactac  10380
aaaaaggatt agactgaacc gaattggtat atagtttaaa caaaacgaat gatttcgact  10440
cattaaatta tgataatcat atttaccaaa tgcccctcat ttacataaat attatactag  10500
catttaccat ctcacttcta ggaatactag tatatcgctc acacctcata tcctccctac  10560
tatgcctaga aggaataata ctatcgctgt tcattatagc tactctcata accctcaaca  10620
cccactccct cttagccaat attgtgccta ttgccatact agtctttgcc gcctgcgaag  10680
cagcggtggg cctagcccta ctagtctcaa tctccaacac atatggccta gactacgtac  10740
ataacctaaa cctactccaa tgctaaaact aatcgtccca caattatat tactaccact  10800 gacatgactt tccaaaaaac acataatttg aatcaacaca accaccccaca gcctaattat  10860 tagcatcatc cctctactat tttttaacca aatcaacaac aacctattta gctgttcccc  10920 aacctttttcc tccgaccccc taacaaccc cctcctaata ctaactaccct gactcctacc  10980 cctcacaatc atggcaagcc aacgccactt atccagtgaa ccactatcac gaaaaaaact  11040
ctacctctct atactaatct ccctacaaat ctccttaatt ataacattca cagccacaga  11100
```

-continued

```
actaatcata ttttatatct tcttcgaaac cacacttatc cccaccttgg ctatcatcac    11160
ccgatgaggc aaccagccag aacgcctgaa cgcaggcaca tacttcctat tctacaccct    11220
agtaggctcc cttcccctac tcatcgcact aatttacact cacaacaccc taggctcact    11280
aaacattcta ctactcactc tcactgccca agaactatca aactcctgag ccaacaactt    11340
aatatgacta gcttacacaa tagctttat agtaaagata cctctttacg gactccactt     11400
atgactccct aaagcccatg tcgaagcccc catcgctggg tcaatagtac ttgccgcagt    11460
actcttaaaa ctaggcggct atggtataat acgcctcaca ctcattctca accccctgac    11520
aaaacacata gcctacccct tccttgtact atccctatga ggcataatta taacaagctc    11580
catctgccta cgacaaacag acctaaaatc gctcattgca tactcttcaa tcagccacat    11640
agccctcgta gtaacagcca ttctcatcca accccctga agcttcaccg gcgcagtcat    11700
tctcataatc gcccacgggc ttacatcctc attactattc tgcctagcaa actcaaacta    11760
cgaacgcact cacagtcgca tcataatcct ctctcaagga cttcaaactc tactcccact    11820
aatagctttt tgatgacttc tagcaagcct cgctaacctc gccttacccc ccactattaa    11880
cctactggga gaactctctg tgctagtaac cacgttctcc tgatcaaata tcactctcct    11940
acttacagga ctcaacatac tagtcacagc cctatactcc ctctacatat ttaccacaac    12000
acaatggggc tcactcaccc accacattaa caacataaaa ccctcattca cacgagaaaa    12060
caccctcatg ttcatacacc tatccccat tctcctccta tccctcaacc ccgacatcat    12120
taccgggttt tcctcttgta aatatagttt aaccaaaaca tcagattgtg aatctgacaa    12180
cagaggctta cgaccccta tttaccgaga aagctcacaa gaactgctaa ctcatgcccc    12240
catgtctaac aacatggctt tctcaacttt taaaggataa cagctatcca ttggtcttag    12300
gccccaaaaa ttttggtgca actccaaata aaagtaataa ccatgcacac tactataacc    12360
accctaaccc tgacttccct aattccccc atccttacca ccctcgttaa ccctaacaaa    12420
aaaaactcat accccccatta tgtaaaatcc attgtcgcat ccacctttat tatcagtctc    12480
ttccccacaa caatattcat gtgcctagac caagaagtta ttatctcgaa ctgacactga    12540
gccacaaccc aaacaaccca gctctcccta agcttcaaac tagactactt ctccataata    12600
ttcatccctg tagcattgtt cgttacatgg tccatcatag aattctcact gtgatatata    12660
aactcagacc caaacattaa tcagttcttc aaatatctac tcatcttcct aattaccata    12720
ctaatcttag ttaccgctaa caacctattc caactgttca tcggctgaga gggcgtagga    12780
attatatcct tcttgctcat cagttgatga tacgcccgag cagatgccaa cacagcagcc    12840
attcaagcaa tcctatacaa ccgtatcggc gatatcggtt tcatcctcgc cttagcatga    12900
tttatcctac actccaactc atgagaccca caacaaatag cccttctaaa cgctaatcca    12960
agcctcaccc cactactagg cctcctccta gcagcagcag gcaaatcagc ccaattaggt    13020
ctccacccct gactccccte agccatagaa ggccccaccc cagtctcagc cctactccac    13080
tcaagcacta tagttgtagc aggaatcttc ttactcatcc gcttccaccc cctagcagaa    13140
aatagcccac taatccaaac tctaacacta tgcttaggcg ctatcaccac tctgttcgca    13200
gcagtctgcg cccttacaca aaatgacatc aaaaaaatcg tagccttctc cacttcaagt    13260
caactaggac tcataatagt tacaatcggc atcaaccaac cacacctagc attcctgcac    13320
atctgtaccc acgccttctt caaagccata ctatttatgt gctccgggtc catcatccac    13380
aaccttaaca atgaacaaga tattcgaaaa ataggaggac tactcaaaac catacctctc    13440
acttcaacct ccctcaccat tggcagccta gcattagcag gaatacctttt cctcacaggt    13500
```

```
ttctactcca aagaccacat catcgaaacc gcaaacatat catacacaaa cgcctgagcc   13560
ctatctatta ctctcatcgc tacctccctg acaagcgcct atagcactcg aataattctt   13620
ctcaccctaa caggtcaacc tcgcttcccc acccttacta acattaacga aaataacccc   13680
accctactaa accccattaa acgcctggca gccggaagcc tattcgcagg atttctcatt   13740
actaacaaca tttcccccgc atcccccttc caaacaacaa tcccctctca cctaaaactc   13800
acagccctcg ctgtcacttt cctaggactt ctaacagccc tagacctcaa ctacctaacc   13860
aacaaactta aaataaaatc cccactatgc acattttatt tctccaacat actcggattc   13920
taccctagca tcacacaccg cacaatcccc tatctaggcc ttcttacgag ccaaaacctg   13980
cccctactcc tcctagacct aacctgacta gaaaagctat tacctaaaac aatttcacag   14040
caccaaatct ccacctccat catcacctca acccaaaaag gcataattaa acttacttc    14100 ctctctttct tcttcccact catcctaacc ctactcctaa tcacataacc tattcccccg   14160
agcaatctca attacaatat atacaccaac aaacaatgtt caaccagtaa ctactactaa   14220
tcaacgccca taatcataca aagcccccgc accaatagga tcctcccgaa tcaaccctga   14280
cccctctcct tcataaatta ttcagcttcc tacactatta aagtttacca caaccaccac   14340
cccatcatac tctttcaccc acagcaccaa tcctacctcc atcgctaacc ccactaaaac   14400
actcaccaag acctcaaccc ctgaccccca tgcctcagga tactcctcaa tagccatcgc   14460
tgtagtatat ccaaagacaa ccatcattcc ccctaaataa attaaaaaaa ctattaaacc   14520
catataacct cccccaaaat tcagaataat aacacacccg accacaccgc taacaatcaa   14580
tactaaaccc ccataaatag gagaaggctt agaagaaaac cccacaaacc ccattactaa   14640
acccacactc aacagaaaca aagcatacat cattattctc gcacggacta caaccacgac   14700
caatgatatg aaaaaccatc gttgtatttc aactacaaga acaccaatga ccccaatacg   14760
caaaactaac cccctaataa aattaattaa ccactcattc atcgacctcc ccaccccatc   14820
caacatctcc gcatgatgaa acttcggctc actccttggc gcctgcctga tcctccaaat   14880
caccacagga ctattcctag ccatgcacta ctcaccagac gcctcaaccg ccttttcatc   14940
aatcgcccac atcactcgag acgtaaatta tggctgaatc atccgctacc ttcacgccaa   15000
tggcgcctca atattcttta tctgcctctt cctacacatc gggcgaggcc tatattacgg   15060
atcatttctc tactcagaaa cctgaaacat cggcattatc ctcctgcttg caactatagc   15120
aacagccttc ataggctatg tcctcccgtg aggccaaata tcattctgag gggccacagt   15180
aattacaaac ttactatccg ccatcccata cattgggaca gacctagttc aatgaatctg   15240
aggaggctac tcagtagaca gtcccaccct cacacgattc tttacctttc acttcatctt   15300
gcccttcatt attgcagccc tagcaacact ccacctccta ttcttgcacg aaacgggatc   15360
aaacaacccc ctaggaatca cctcccattc cgataaaatc accttccacc cttactacac   15420
aatcaaagac gccctcggct tacttctctt ccttctctcc ttaatgacat taacactatt   15480
ctcaccagac ctcctaggcg acccagacaa ttatacccta gccaacccct aaacaccccc   15540
tccccacatc aagcccgaat gatatttcct attcgcctac acaattctcc gatccgtccc   15600
taacaaacta ggaggcgtcc ttgccctatt actatccatc ctcatcctag caataatccc   15660
catcctccat atatccaaac aacaaagcat aatatttcgc ccactaagcc aatcacttta   15720
ttgactccta gccgcagacc tcctcattct aacctgaatc ggaggacaac cagtaagcta   15780 ccctttacc atcattggac aagtagcatc cgtactatac ttcacaacaa tcctaatcct   15840
```

```
aataccaact atctccctaa ttgaaaacaa aatactcaaa tgggcctgtc cttgtagtat    15900
aaactaatac accagtcttg taaaccggag atgaaaacct ttttccaagg acaaatcaga    15960
gaaaaagtct ttaactccac cattagcacc caaagctaag attctaattt aaactattct    16020
ctgttctttc atggggaagc agatttgggt accaccaag tattgactca cccatcaaca     16080
accgctatgt atttcgtaca ttactgccag ccaccatgaa tattgtacgg taccataaat    16140
acttgaccac ctgtagtaca taaaaaccca atccacatca aaaccccctc ccatgcttac    16200
caagcaagta cagcaatcaa ccctcaacta tcacacatca actgcaactc caaagccacc    16260
cctcacccac taggatacca acaaacctac ccacccttaa cagtacatag tacataaagc    16320
catttaccgt acatagcaca ttacagtcaa atccttctc gtccccatgg atgacccccc    16380
tcagataggg gtcccttgac caccatcctc cgtgaaatca atatcccgca caagagtgct    16440
actctcctcg ctccgggccc ataacacttg ggggtagcta aagtgaactg tatccgacat    16500
ctggttccta cttcagggtc ataaagccta aatagcccac acgttcccct taaataagac    16560
atcacgatg                                                            16569
```

<210> SEQ ID NO 4
<211> LENGTH: 29
<212> TYPE: DNA
<213> ORGANISM: Artificial
<220> FEATURE:
<223> OTHER INFORMATION: Forward deletion detection primer

<400> SEQUENCE: 4
ttggtgcaac tccaaagcca cccctcacc                                       29

<210> SEQ ID NO 5
<211> LENGTH: 19
<212> TYPE: DNA
<213> ORGANISM: artificial
<220> FEATURE:
<223> OTHER INFORMATION: Reverse deletion detection primer.

<400> SEQUENCE: 5
aggatggtgg tcaagggac                                                  19

<210> SEQ ID NO 6
<211> LENGTH: 31
<212> TYPE: DNA
<213> ORGANISM: Artificial
<220> FEATURE:
<223> OTHER INFORMATION: Forward deletion detection primer

<400> SEQUENCE: 6
cccaaaaatt ttggtgcaac tccaaagcca c                                    31

<210> SEQ ID NO 7
<211> LENGTH: 12
<212> TYPE: DNA
<213> ORGANISM: Homo sapiens

<400> SEQUENCE: 7
tgcaactcca aa                                                         12

<210> SEQ ID NO 8
<211> LENGTH: 16
<212> TYPE: DNA
<213> ORGANISM: Homo sapiens

<400> SEQUENCE: 8

```
ttggtgcaac tccaaa                                           16

<210> SEQ ID NO 9
<211> LENGTH: 13
<212> TYPE: DNA
<213> ORGANISM: Homo sapiens

<400> SEQUENCE: 9
gccacccctc acc                                              13
```

MITOCHONDRIAL DNA DELETION BETWEEN ABOUT RESIDUES 12317-16254 FOR USE IN THE DETECTION OF CANCER

CROSS-REFERENCE TO RELATED APPLICATIONS

This application is a Continuation of U.S. patent application Ser. No. 15/188,604, filed Jun. 21, 2016, which is a Continuation of U.S. patent application Ser. No. 14/489,119, filed Sep. 17, 2014, which is a Continuation of U.S. patent application Ser. No. 13/745,204, filed Jan. 18, 2013, which is a Continuation of U.S. patent application Ser. No. 12/742,032, filed Aug. 25, 2010, which is a National Stage Entry of PCT/CA2008/001956, filed Nov. 10, 2008, which claims priority from U.S. Application No. 61/002,637, filed Nov. 9, 2007. The entire contents of each of the aforementioned applications are incorporated herein by reference as if set forth in their entirety.

SEQUENCE LISTING

A computer readable text file, entitled "Sequence Listing.txt", created on Apr. 5, 2018, with a file size of about 33 kb contains the sequence listing for this application and is hereby incorporated by reference in its entirety.

FIELD OF THE INVENTION

The present invention pertains to the field of mitochondrial genomics. In particular it is related to the detection of human mitochondrial genome mutations and their utility as an indicators of cancer.

BACKGROUND OF THE INVENTION

Mitochondrial DNA as a Diagnostic Tool

Mitochondrial DNA (mtDNA) sequence dynamics are important diagnostic tools. Mutations in mtDNA are often preliminary indicators of developing disease, often associated with nuclear mutations, and act as biomarkers specifically related to: disease, such as but not limited to, tissue damage and cancer from smoking and exposure to second hand tobacco smoke (Lee et al., 1998; Wei, 1998); longevity, based on accumulation of mitochondrial genome mutations beginning around 20 years of age and increasing thereafter (von Wurmb, 1998); metastatic disease caused by mutation or exposure to carcinogens, mutagens, ultraviolet radiation (Birch-Machin, 2000); osteoarthritis; cardiovascular, Alzheimer, Parkinson disease (Shoffner et al., 1993; Sherratt et al., 1997; Zhang et al, 1998); age associated hearing loss (Seidman et al., 1997); optic nerve degeneration and cardiac dysrhythmia (Brown et al., 1997; Wallace et al., 1988); chronic progressive external exophthalmoplegia (Taniike et al., 1992); atherosclerosis (Bogliolo et al., 1999); papillary thyroid carcinomas and thyroid tumours (Yeh et al., 2000); as well as others (e.g. Naviaux, 1997; Chinnery and Turnbull, 1999).

Mutations at specific sites of the mitochondrial genome can be associated with certain diseases. For example, mutations at positions 4216, 4217 and 4917 are associated with Leber's Hereditary Optic Neuropathy (LHON) (Mitochondrial Research Society; Huoponen (2001); MitoMap). A mutation at 15452 was found in 5/5 patients to be associated with ubiquinol cytochrome c reductase (complex III) deficiency (Valnot et al. 1999).

Specifically, these mutations or alterations include point mutations (transitions, transversions), deletions (one base to thousands of bases), inversions, duplications, (one base to thousands of bases), recombinations and insertions (one base to thousands of bases). In addition, specific base pair alterations, deletions, or combinations thereof have been found to be associated with early onset of prostate, skin, and lung cancer, as well as aging (e.g. Polyak et al., 1998), premature aging, exposure to carcinogens (Lee et al., 1998), etc.

Prostate Cancer

Prostate cancer is a frequently diagnosed solid tumour that most likely originates in the prostate epithelium (Huang et al. 1999). In 1997, nearly 10 million American men were screened for prostate specific antigen (PSA), the presence of which suggests prostate cancer (Woodwell, 1999). Indeed, this indicates an even higher number of men screened by an initial digital rectal exam (DRE). In the same year, 31 million men had a DRE (Woodwell, 1999). Moreover, the annual number of newly diagnosed cases of prostate cancer in the United States is estimated at 179,000 (Landis et al., 1999). It is the second most commonly diagnosed cancer and second leading cause of cancer mortality in Canadian men. In 1997 prostate cancer accounted for 19,800 of newly diagnosed cancers in Canadian men (28%) (National Cancer Institute of Canada). It is estimated that 30% to 40% of all men over the age of forty-nine (49) have some cancerous prostate cells, yet only 20% to 25% of these men have a clinically significant form of prostate cancer (SpringNet—CE Connection, internet, www.springnet.com/ce/j803a.htm). Prostate cancer exhibits a wide variety of histological behaviour involving both endogenous and exogenous factors, i.e. socio-economic situations, diet, geography, hormonal imbalance, family history and genetic constitution (Konishi et al. 1997; Hayward et al. 1998). Although certain mtDNA alterations have been previously associated with prostate cancer, the need exists for further markers for the detection of prostate cancer.

Breast Cancer

Breast cancer is a cancer of the glandular breast tissue and is the fifth most common cause of cancer death. In 2005, breast cancer caused 502,000 deaths (7% of cancer deaths; almost 1% of all deaths) worldwide (World Health Organization Cancer Fact Sheet No. 297). Among women worldwide, breast cancer is the most common cancer and the most common cause of cancer death (World Health Organization Cancer Fact Sheet No. 297). Although certain mtDNA alterations have been previously associated with breast cancer, for example in Parrella et al. (Cancer Research: 61, 2001), the need exists for further markers for the detection of breast cancer.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention pertains to mitochondrial DNA mutations for use in the detection of cancer. In accordance with an aspect of the present invention, there is provided a method of detecting a cancer in an individual comprising:
  a) obtaining a biological sample from the individual;
  b) extracting mitochondrial DNA (mtDNA) from the sample;

c) quantifying the amount of mtDNA in the sample having a deletion in the mtDNA sequence between about residue 12317 and about residue 16254 of the human mtDNA genome; and d) comparing the amount of mtDNA in the sample having the deletion to at least one known reference value.

In accordance with another aspect of the present invention, there is provided a method of monitoring an individual for the development of a cancer comprising:

a) obtaining a biological sample;

b) extracting mitochondrial DNA (mtDNA) from the sample;

c) quantifying the amount of mtDNA in the sample having a deletion in the mtDNA sequence between about residue 12317 and about residue 16254 of the human mtDNA genome; and d) repeating steps a) to c) over a duration of time;

wherein an increasing level of the deletion over the duration of time is indicative of cancer.

In accordance with another aspect of the present invention, there is provided a method of detecting a cancer in an individual comprising:

a) obtaining a biological sample from the individual;

b) extracting mitochondrial DNA (mtDNA) from the sample;

c) quantifying the amount of mtDNA in the sample having a sequence corresponding to the sequence as set forth in SEQ ID NO: 1 or SEQ ID NO: 2; and d) comparing the amount of mtDNA in the sample corresponding to SEQ ID NO: 1 or SEQ ID NO: 2 to at least one known reference value.

In accordance with another aspect of the present invention, there is provided a diagnostic kit for carrying out the method of the invention comprising:

(a) material for collecting one or more biological samples; and (b) suitable primers and reagents for detecting the mtDNA deletion.

In one aspect, there is provided a method of detecting breast or prostate cancer, or a genetic predisposition to breast or prostate cancer, in a human subject, the cancer being characterized by an elevated amount of mitochondrial DNA (mtDNA) having a deletion of 3926 base pairs within a region of mtDNA between nucleotides 12317 and 16254, with respect to SEQ ID NO: 3, of the human mtDNA genome, the method comprising:

a) contacting mtDNA extracted from a biological sample from the subject with at least one binding agent that specifically binds to a sequence of mtDNA having a spliced region after removal of the deletion;

b) quantifying the amount of mtDNA having the deletion by quantifying the amount of mtDNA bound to the at least one binding agent; and, c) detecting the cancer or the predisposition to cancer where the quantified amount of mtDNA having the deletion is elevated in relation to at least one known reference value.

In another aspect, there is provided a method of detecting breast or prostate cancer, or a genetic predisposition to breast or prostate cancer, in a human subject, the cancer being characterized by an elevated amount of mitochondrial DNA (mtDNA) having a deletion in the human mtDNA genome, the deletion having a nucleotide sequence as set forth in SEQ ID NO: 1 or SEQ ID NO: 2, the method comprising:

a) contacting mtDNA extracted a biological sample from the subject with at least one binding agent that specifically binds to: i) a sequence of mtDNA having a spliced region after removal of the deletion; or ii) to a sequence of mtDNA comprising the rejoining site of the deletion sequence of SEQ ID NO: 1 or SEQ ID NO: 2 after the deletion sequence has re-circularized;

b) quantifying the amount of mtDNA having the deletion by quantifying the amount of mtDNA bound to the at least one binding agent; and, c) detecting the cancer or the predisposition to cancer where the quantified amount of mtDNA having the deletion is elevated in relation to at least one known reference value.

BRIEF DESCRIPTION OF THE FIGURES

These and other features of the invention will become more apparent in the following detailed description in which reference is made to the appended drawings.

DETAILED DESCRIPTION OF THE INVENTION

Figure 1:
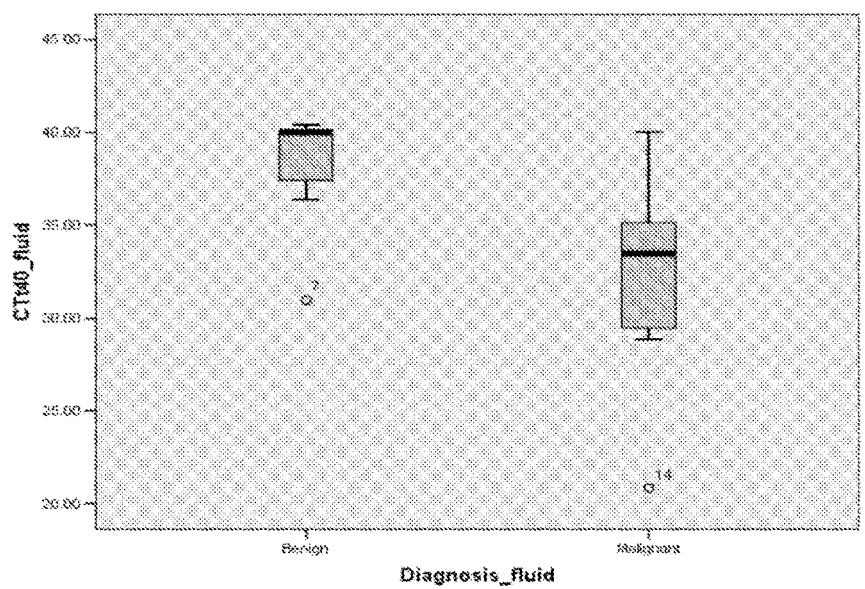
FIG. 1 is a graph showing cycle threshold as related to Example 1.

The present invention provides methods of predicting, diagnosing and monitoring cancer. The methods comprise obtaining one or more biological samples, extracting mitochondrial DNA (mtDNA) from the samples, quantifying the amount of a mitochondrial mutation in the samples and comparing the quantity of the mutation in a sample with a reference value. In this regard, the methods provide a comprehensive tool for determining disease onset and for assessing the predisposition of an individual to cancer. The methods also allow for the monitoring of an individual's risk factors over time and/or for monitoring a patient's response to therapeutic agents and treatment regimes.

Definitions

Unless defined otherwise, all technical and scientific terms used herein have the same meaning as commonly understood by one of ordinary skill in the art to which this invention belongs.

As used herein, the term "about" refers to an understood variation from the stated value. It is to be understood that such a variation is always included in any given value provided herein, whether or not it is specifically referred to.

As defined herein, "biological sample" refers to a tissue or bodily fluid containing cells from which mtDNA can be obtained. For example, the biological sample can be derived from tissue such as breast or prostate tissue, or from blood, saliva, cerebral spinal fluid, sputa, urine, mucous, synovial fluid, peritoneal fluid, amniotic fluid and the like. The biological sample may be a surgical specimen or a biopsy specimen. The biological sample can be used either directly as obtained from the source or following a pre-treatment to modify the character of the sample. Thus, the biological sample can be pre-treated prior to use by, for example, preparing plasma or serum from blood, disrupting cells, preparing liquids from solid materials, diluting viscous fluids, filtering liquids, distilling liquids, concentrating liquids, inactivating interfering components, adding reagents, and the like.

As used herein, "cycle threshold" ($C_T$) is the point at which target amplification using real-time PCR rises above background, as indicated by a signal such as a fluorescence signal. The $C_T$ is inversely related to the quantity of the sequence being investigated.

As used herein, "diagnostic" or "diagnosing" means using the presence or absence of a mutation or combination of mutations as a factor in disease diagnosis or management. The detection of the mutation(s) can be a step in the diagnosis of a disease.

As used herein, "deletion" means removal of a region of mtDNA from a contiguous sequence of mtDNA. Deletions can range in size from one base to thousands of bases or larger.

As used herein, "mitochondrial DNA" or "mtDNA" is DNA present in mitochondria.

As used herein, "mutation" encompasses any modification or change in mitochondrial DNA from the wild type sequence, including without limitation point mutations, transitions, insertions, transversions, translocations, deletions, inversions, duplications, recombinations or combinations thereof. The modification or change of the sequence can extend from a single base change to the addition or elimination of an entire DNA fragment.

As defined herein, "sensitivity" refers to the fraction of true positives (true positive rate) results obtained using the method of the present invention.

As defined herein, "specificity" refers to the fraction of false positives (false positive rate) results obtained using the method of the present invention.

The terms "therapy" and "treatment," as used interchangeably herein, refer to an intervention performed with the intention of improving a subject's status. The improvement can be subjective or objective and is related to ameliorating the symptoms associated with, preventing the development of, or altering the pathology of a disease. Thus, the terms therapy and treatment are used in the broadest sense, and include the prevention (prophylaxis), moderation, reduction, and curing of a disease, at various stages. Preventing deterioration of a subject's status is also encompassed by the term. Subjects in need of therapy/treatment thus include those already having the disease, as well as those prone to, or at risk of developing, the disease, and those in whom the disease is to be prevented.

Assays for Predicting, Diagnosing and Monitoring Cancer
Assay for Detection of Mitochondrial Mutation Mitochondrial DNA (mtDNA) dynamics are an important diagnostic tool. Mutations in mtDNA are often preliminary indicators of developing disease and may act as biomarkers indicative of risk factors associated with disease onset. As discussed herein, measuring the level of mitochondrial DNA aberration in a biological sample can determine the presence of one or more cancers and identify the potential risk or predisposition of a patient to one or more cancers. Furthermore, measurement of mtDNA at regular intervals can provide health care professionals with a real-time, quantitative monitoring tool for measuring the progression of a patient over time and/or as an assessment for treatment recommendations in order to determine their effectiveness in preventing or treating cancer.

The present invention, therefore, provides methods for predicting, diagnosing or monitoring cancer, comprising obtaining one or more biological samples, extracting mitochondrial DNA (mtDNA) from the samples, and assaying the samples for mitochondrial mutation by: quantifying the amount of an mtDNA aberration in the sample and comparing the level of the aberration with a reference value. As would be understood by those of skill in the art, the reference value is based on whether the method seeks to predict, diagnose or monitor cancer. Accordingly, the reference value may relate to mtDNA data collected from one or more known non-cancerous biological samples, from one or more known cancerous biological samples, and/or from one or more biological samples taken over time. These reference values are used for comparison with the mtDNA data collected from the one or more biological samples wherein, for example, a similar or elevated amount of deletion in the biological sample compared to the reference sample is indicative of a predisposition to or the onset of cancer, or wherein an increasing level of the deletion over time is indicative of cancer onset.

In accordance with an aspect of the invention, the methods for predicting, monitoring and diagnosing cancer comprise an assay for detecting and quantifying one or more mitochondrial mutations. In accordance with one embodiment of the invention, the mutation is an mtDNA deletion. In accordance with another embodiment, the mutation is an mtDNA deletion of 3926 bp of mtDNA (referred to herein as "the 4 kb deletion" or "4 kb sequence"). In accordance with yet another embodiment, the mutation is an mtDNA deletion having the sequence as set forth in SEQ ID NO:1 or SEQ ID NO:2, there being no difference between SEQ ID NO: 1 and SEQ ID NO: 2 when in circular form.

The 4 kb deletion spans approximately nucleotides 12317 and 16254 of the human mtDNA genome. The human mtDNA genome is listed herein as SEQ ID NO:3 (Genbank accession no. AC_000021). The 4 kb deletion is characterized by direct flanking repeats 12 bp in size, with the repeats located at positions 12317-12328 and 16243 to 16254. The repeat sequence is 5'-TGCAACTCCAAA-3' (SEQ ID NO: 7). Thus, in accordance with one embodiment of the invention, the mutation is an mtDNA deletion of between about residue 12317 and about residue 16254 of the human mtDNA genome.

The inventors have determined, as provided by way of example below, that this deletion is associated with cancer and in particular prostate and breast cancer. Therefore, such deletion provides an accurate biomarker and, therefore, a valuable tool for the detection, diagnosis, or monitoring of cancer in at least these tissues.

The deletion results in the creation of two deletion monomers, one of 4 kb in size (small sublimon) and one of approximately 12.5 kb in size (large sublimon). The occurrence of the deletion may be detected by either identifying the presence of the small sublimon or the large sublimon, the 4 kb or 12.5 kb sequence respectively.

Exemplary methods for assaying the mitochondrial mutation are provided in the Example section. Extraction of mtDNA from a sample may be undertaken using any suitable known method. MtDNA extraction is followed by amplification of all or a region of the mitochondrial genome, and may include sequencing of the mitochondrial genome, as is known in the art and described, for example, in Current Protocols in Molecular Biology (Ausubel et al., John Wley & Sons, New York, 2007). Likewise, methods for detecting the presence of mutations in the mtDNA can be selected from suitable techniques known to those skilled in the art. For example, analyzing mtDNA can comprise sequencing the mtDNA, amplifying mtDNA by PCR, Southern, Northern, Western South-Western blot hybridizations, denaturing HPLC, hybridization to microarrays, biochips or gene chips, molecular marker analysis, biosensors, melting temperature profiling or a combination of any of the above.

Any suitable means to sequence mitochondrial DNA may be used. Preferably, mtDNA is amplified by PCR prior to sequencing. The method of PCR is well known in the art and may be performed as described in Mullis and Faloona, 1987, Methods Enzymol., 155: 335. PCR products can be sequenced directly or cloned into a vector which is then placed into a bacterial host. Examples of DNA sequencing methods are found in Brumley, R. L. Jr. and Smith, L. M., 1991, Rapid DNA sequencing by horizontal ultrathin gel electrophoresis, Nucleic Acids Res. 19:4121-4126 and Luckey, J. A., et al, 1993, High speed DNA sequencing by capillary gel electrophoresis, Methods Enzymol. 218: 154-172. The combined use of PCR and sequencing of mtDNA is described in Hopgood, R., et al, 1992, Strategies for automated sequencing of human mtDNA directly from PCR products, Biotechniques 13:82-92 and Tanaka, M. et al, 1996, Automated sequencing of mtDNA, Methods Enzymol. 264: 407-421.

Although real-time quantitative PCR methods, as described in the examples below, represent the preferred means for detecting and quantifying the presence or absence of the 4 kb deletion, other methods would be well known to an individual of skill in the art and could be utilized as indicated above. In addition, quantification of the deletion could be made using Bio-Rad's Bioplex™ System and Suspension Array technology. Generally, the method requires amplification and quantification of sequences using any known methods.

The following primer sequences are examples of primers that may be used for the detection of the 4 kb deletion:

```
4 forward (binds to bases 12313-12328

(TTGGTGCAACTCCAAA; SEQ ID NO: 8)/16255-16267

(GCCACCCCTCACC; SEQ ID NO: 9)

of the human mtDNA genome)
                                    (SEQ ID NO: 4)
5'-TTGGTGCAACTCCAAAGCCACCCCTCACC-3';

4 reverse (binds to bases 16391-16409 of the
human mtDNA genome)
                                    (SEQ ID NO: 5)
5'-AGGATGGTGGTCAAGGGAC-3'.
```

Figure 5:
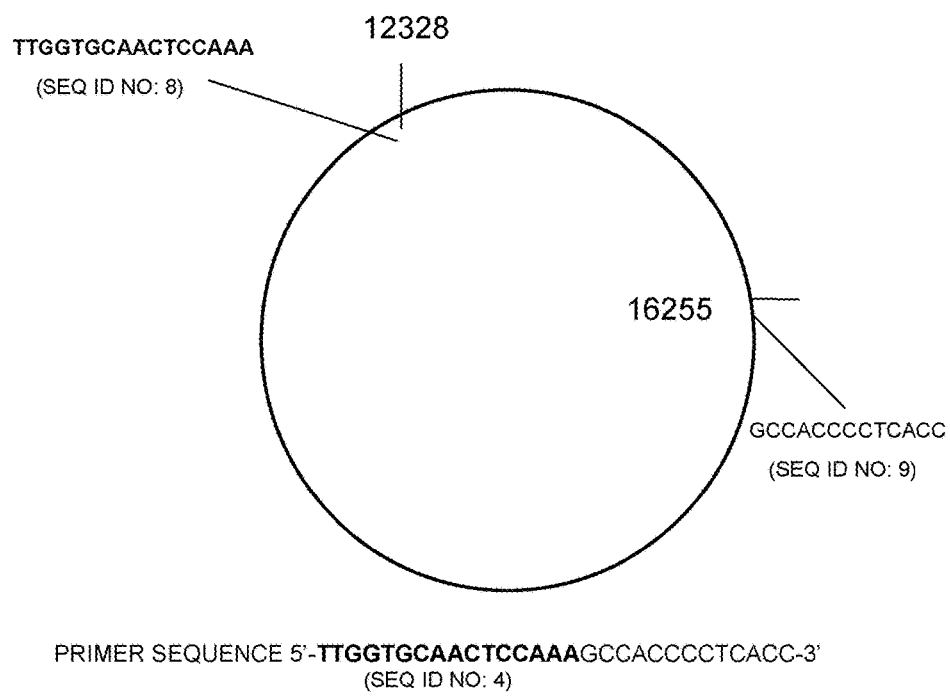
FIG. 5 is a schematic diagram showing the design and sequence (SEQ ID NO: 4) of a primer useful for the detection of the 4 kb deletion.

In one embodiment of the present invention, a pair of amplification primers are used to amplify a target region indicative of the presence of the 4 kb deletion. In this embodiment, one of the pair of amplification primers overlaps a spliced region of mtDNA after deletion of the 4 kb sequence has occurred and the mtDNA has reformed as a circular mtDNA molecule (e.g. a splice at a position between 12328 and 16255 of the mtDNA genome). Therefore, extension of the overlapping primer can only occur if the 4 kb section is deleted. FIG. 5 is a schematic diagram showing the design and sequence of the primer (i.e. SEQ ID NO: 4).

In another embodiment of the present invention, a pair of amplification primers are used to amplify a target region associated with the deleted 4 kb sequence. The deleted 4 kb sequence, upon deletion, may reform as a circular mtDNA molecule. In this embodiment, one of the pair of amplification primers overlaps the rejoining site of the ends of the 4 kb sequence. Thus, an increase in the amount of the 4 kb molecule detected in a sample is indicative of cancer.

In still another embodiment of the present invention, the breakpoint of the deletion is unknown thereby resulting in two possibilities for primer location. In this embodiment, two separate forward primers may be designed to amplify the target region associated with the deleted 4 kb sequence. The following primer sequences are examples of those that may be used for the detection of the 4 kb deletion in this scenario:

```
Forward Primers:
Primer A (binds to bases 12313-12328/16255-16267
of the human mtDNA genome)
                                    (SEQ ID NO: 4)
5'-TTGGTGCAACTCCAAAGCCACCCCTCACC-3';

Primer B (binds to bases 12302-12316 of the human
mtDNA genome)
                                    (SEQ ID NO: 6)
5'-CCCAAAAATTTTGGTGCAACTCCAAAGCCAC-3'.

Reverse Primers:
Primer C (binds to bases 16391-16409 of the human
mtDNA genome)
                                    (SEQ ID NO: 5)
5'-AGGATGGTGGTCAAGGGAC-3'.
```

As would be understood by a person of skill in the art, the forward primers A or B can be used with reverse primer C to create PCR products that are useful in qPCR assays.

Biological Sample

The present invention provides for diagnostic tests which involve obtaining or collecting one or more biological samples. In the context of the present invention, "biological sample" refers to a tissue or bodily fluid containing cells from which mtDNA can be obtained. For example, the biological sample can be derived from tissue including, but not limited to, breast, prostate, nervous, muscle, heart, stomach, colon tissue and the like; or from blood, saliva, cerebral spinal fluid, sputa, urine, mucous, synovial fluid, peritoneal fluid, amniotic fluid and the like. The biological sample may be obtained from a cancerous or non-cancerous tissue and may be a surgical specimen or a biopsy specimen.

The biological sample can be used either directly as obtained from the source or following a pre-treatment to modify the character of the sample. Thus, the biological sample can be pre-treated prior to use by, for example, preparing plasma or serum from blood, disrupting cells, preparing liquids from solid materials, diluting viscous fluids, filtering liquids, distilling liquids, concentrating liquids, inactivating interfering components, adding reagents, and the like.

One skilled in the art will understand that more than one sample type may be assayed at a single time (i.e. for the detection of more than one cancer). Furthermore, where a course of collections are required, for example, for the monitoring of risk factors or cancer over time, a given sample may be diagnosed alone or together with other sample taken throughout the test period. In this regard, biological samples may be taken once only, or at regular intervals such as biweekly, monthly, semi-annually or annually.

One of skill will also appreciate that mitochondrial DNA targets are in much greater abundance (approximately 1000 fold greater) than nucleic acid targets and as such sample sizes comprising extremely low yields of nucleic acids would be suitable for use with the present invention.

Applications for Predicating, Diagnosing and Monitoring Cancer

Diagnosing and Monitoring Cancer

The prevalence of cancer in most tissue types and age groups necessitates the availability of a tool to not only detect the presence of cancer, but also to monitor the success and appropriateness of preventative measures and therapies being advised to prevent onset, progression and spread of the disease. Measuring the level of mitochondrial DNA deletions in one or more biological samples of an individual can provide initial diagnosis of risk factors, cancer and/or stages of the disease.

The system and method of the present invention, for example, may be used to detect cancer at an early stage, and before any histological abnormalities. Furthermore, sample testing at regular intervals such as biweekly, monthly, semi-annually or annually (or any other suitable interval) can provide health care professionals with a real-time, quantitative monitoring tool to compare against treatment recommendations to determine their effectiveness in preventing or treating the disease.

Turning now to the examples, in one embodiment the present invention may be used for detecting the presence of pre-neoplasia, neoplasia and progression towards potential malignancy of prostate cancer and breast cancer. In one aspect, the present invention involves the detection and quantification of the 4 kb mtDNA deletion for the detection, diagnosis, and/or monitoring of cancer. In this method, mtDNA is extracted from a biological sample (for example body tissue, or body fluids such as urine, prostate massage fluid). The extracted mtDNA is then tested in order to determine the levels (i.e. quantity) of the 4 kb deletion in the sample. In tests conducted by the present inventors, the levels of the deletion were found to be elevated in samples obtained from subjects with cancer when compared to samples obtained from subjects without cancer. Based on the information and data supplied below, the inventors have concluded that elevated levels of the 4 kb deletion in human mtDNA is indicative of cancer.

In another embodiment, samples of, for instance prostate tissue, prostate massage fluid, urine or breast tissue, are obtained from an individual and tested over a period of time (e.g. years) in order to monitor the genesis or progression of cancer. Increasing levels of the 4 kb deletion over time could be indicative of the beginning or progression of cancer.

One of ordinary skill in the art will appreciate that analysing one or more biological samples from an individual for quantification of a mitochondrial DNA target provides a means for a health care worker to monitor the effectiveness of treatment regimes. One of ordinary skill will also appreciate the utility of mtDNA analysis for use by health care providers in identifying (and providing recommendations for) lifestyle habits, such as poor diet and exercise, or activities that cause over exposure of an individual to known carcinogens (e.g. tobacco, pollutants).

Another aspect of the invention provides methods for confirming or refuting the results of a cancer biopsy test from a biopsy sample (e.g. prostate or breast cancer), comprising: obtaining non-cancerous tissue from a biopsy sample; and detecting and quantifying the amount of the 4 kb mtDNA deletion in the non-diseased tissue.

Determining Genetic Predisposition to Cancer

In order to fully evaluate an individual's risk of one or more cancers it is imperative that health care providers are provided with as much information as possible to understand and communicate their patient's risk factors. The utilization of the present invention to determine the level of mtDNA aberration will not only prove helpful in assessing an individual's susceptibility to one or more cancers, it provides a valuable tool to identify patients with greater risk who are potentially in need of more aggressive monitoring and treatment measures.

In this regard, the various examples provided below illustrate a difference in the amount of mtDNA having the 4 kb deletion between samples obtained from subjects having cancer, and subjects without cancer. The amount of the 4 kb deletion was found to be higher in the samples obtained from subjects having cancer. This determination was made by comparing the amount of the 4 kb deletion in the samples from known cancer cells and/or known non-cancer cells.

As such, the inventors determined that screening of biological samples would prove useful in identifying an individual's predisposition to one or more cancers. Thus, in accordance with one embodiment of the present invention there is provided a method for screening individuals for cancer from one or more biological samples comprising: obtaining the one or more samples, and detecting and quantifying the level of the 4 kb mtDNA deletion in the samples. In a specific embodiment of the invention, there is provided a method for screening individuals for prostate or breast cancer from a body fluid or tissue sample comprising; obtaining the body fluid or tissue sample, and detecting and quantifying the level of the 4 kb mtDNA deletion in the body fluid or tissue sample.

Age related accumulation of the 4 kb mtDNA deletion may also predispose an individual to, for example, prostate cancer or breast cancer, which is prevalent in middle aged and older men, and middle aged and older women, respectively. Similarly, an accumulation of the 4 kb mtDNA deletion may be associated with a particular lifestyle based on an individual's diet, exercise habits, and exposure to known carcinogens. Thus, in accordance with one aspect of the invention, a method is provided wherein regular cancer screening may take place by monitoring over time the amount of the 4 kb deletion in one or more biological samples, non-limiting examples of which include breast and prostate tissues or body fluids such as prostate massage fluid, or urine.

Evaluation of Therapeutic Agents

The method of the present invention may also be used for screening potential therapeutic agents for use in cancer treatment or for monitoring the therapeutic effect of such agents. The method of the present invention may be used to measure various biomarkers associated with the cancers identified herein. The ability to assess the level of DNA damage in any biological sample at any time point provides the foundation for a unique and informative screening test for an individual's health and to assess the safety and efficacy of existing and new therapeutic agents and treatment regimes. Furthermore, by identifying the specific genetic changes underlying a subject's state of health, it may be readily determined whether and to what extent a patient will respond to a particular therapeutic agent or regime.

Kits

The present invention provides diagnostic/screening kits for use in a clinical environment. Such kits could not only include one or more sampling means, but other materials necessary for the identification of mtDNA mutations.

The kits can optionally include reagents required to conduct a diagnostic assay, such as buffers, salts, detection reagents, and the like. Other components, such as buffers and solutions for the isolation and/or treatment of a biological sample, may also be included in the kit. One or more of the components of the kit may be lyophilised and the kit may further comprise reagents suitable for the reconstitution of the lyophilised components.

Where appropriate, the kit may also contain reaction vessels, mixing vessels and other components that facilitate the preparation of the test sample. The kit may also optionally include instructions for use, which may be provided in paper form or in computer-readable form, such as a disc, CD, DVD or the like.

In one aspect of the invention there is provided a kit for diagnosing cancer comprising means for extraction of mtDNA, primers, reagents and instructions.

In another aspect of the invention there is provided a kit for diagnosing cancer, for example prostate or breast cancer, comprising means for extraction of mtDNA, primers having the nucleic acid sequences recited in SEQ ID NOs: 4 and 5, reagents and instructions.

In another aspect of the invention there is provided a kit for diagnosing cancer, for example prostate or breast cancer, comprising means for extraction of mtDNA, primers having the nucleic acid sequences recited in SEQ ID NOs: 6 and 5, reagents and instructions.

To gain a better understanding of the invention described herein, the following examples are set forth. It will be understood that these examples are intended to describe illustrative embodiments of the invention and are not intended to limit the scope of the invention in any way.

EXAMPLES

Example 1

Association of Prostate Cancer with 4 kb Deletion in Human mtDNA

Urine samples were collected from five patients who had been diagnosed with prostate cancer and five who had a needle biopsy procedure which was unable to detect prostate malignancy. These samples were collected following a digital rectal exam (DRE) to facilitate the collection of prostate cells.

Upon receipt of the samples a 5 ml aliquot was removed and then 2 mls were centrifuged at 14,000×g to form a pellet. The supernatant was removed and discarded.

Pellets were resuspended in 200 ul phosphate buffered saline solution. Both the resuspended pellet and the whole urine sample were subjected to a DNA extraction procedure using the QiaAMP DNA Mini Kit (Qiagen P/N 51304) according to the manufacturer's directions. The resulting DNA extracts were then quantified using a NanoDrop ND-1000 Spectrophotometer and normalized to a concentration of 0.1 ng/ul.

Samples were analyzed by quantitative real-time PCR with the 4 kb deletion specific primers according to the following:

1×iQ SYBR Green Supermix (Bio-Rad product no. 170-8880)

100 nmol forward primer (5'-TTGGTGCAACTC-CAAAGCCACCCCTCACC-3') (SEQ ID NO: 4)

100 nmol reverse primer (5'-AGGATGGTGGT-CAAGGGAC-3') (SEQ ID NO: 5)

1 ng template DNA in a 25 ul reaction

Reactions were cycled on an Opticon 2 DNA Engine (Bio-Rad Canada) according to the following protocol:

1. 95° C. for 3 minutes
2. 95° C. for 30 seconds
3. 69° C. for 30 seconds
4. 72° C. for 30 seconds
5. Plate Read
6. Repeat steps 2-5 44 times
7. 72° C. for 10 minutes
8. Melting Curve from 50° C. to 105° C., read every 1° C., hold for 3 seconds
9. 10° C. Hold Results Results from the urine pellet did not yield significant differences in the mean cycle threshold observed or a useful cutoff point. However, the results from the whole urine sample did yield significant differences as provided below.

Tables 1 and 2, and FIG. 1 show the difference in the mean $C_T$ scores for urine samples from subjects having prostate malignant tissue and benign tissue at the 0.04 significance level.

TABLE 1

Mean Values for $C_T$ scores: Urine Samples

|  | N | Mean | Std. Deviation | Std. Error Mean |
|---|---|---|---|---|
| Benign | 7 | 38.0357 | 3.40974 | 1.288876 |
| Malignant | 7 | 31.9300 | 6.12583 | 2.31534 |

TABLE 2

Significance Test for Mean $C_T$ scores
Independent Samples Test

| CTt40 | Levene's Test for Equality of Variances | | Test for Equality Means | | | | | | |
|---|---|---|---|---|---|---|---|---|---|
| fluid | F | Sig. | t | df | Sig. (2-tailed) | Mean Diff. | Std. Error Diff. | 95% Confidence Interval of the Difference Lower | Upper |
| Equal variances assumed | 1.707 | .216 | 2304 | 12 | .040 | 610571 | 264985 | .33218 | 11.87925 |
| Equal variances not assumed |  |  | 2304 | 9392 | .046 | 610571 | 264985 | .14927 | 12.06215 |

Figure 2:
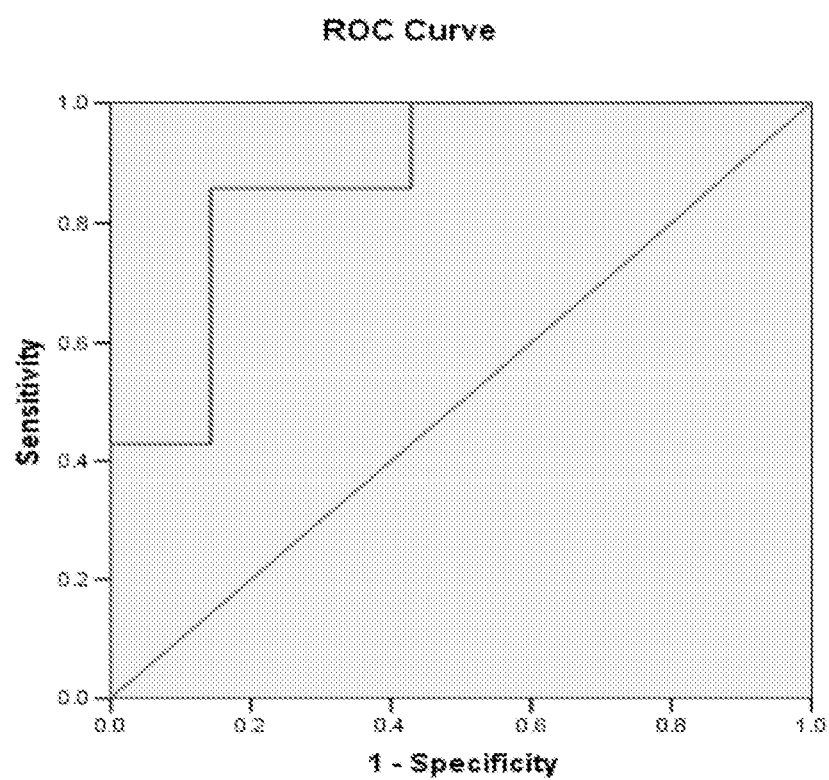
FIG. 2 shows a ROC curve illustrating the specificity and sensitivity of one embodiment of the present invention.

Tables 3 and 4, and FIG. 2 illustrate that when using a cut-off cycle threshold of 36.255 the sensitivity of the assay for prostate cancer is 86% and the specificity is 86%.

FIG. 2 is a Receiver Operating Characteristic (ROC) curve illustrating the specificity and sensitivity of the 4 kb mtDNA deletion as a marker for prostate cancer when testing urine. These results were obtained using a cutoff $C_T$ of 36.255. The sensitivity of the marker at this $C_T$ is 86%, while the specificity is 86%.

The determination of the cutoff $C_T$ of 36.255 is shown in Table 3. The results listed in Table 3 show that a cutoff $C_T$ of 36.255 provided the highest sensitivity and specificity.

The accuracy of the test depends on how well the test separates the group being tested into those with and without the prostate cancer. Accuracy is measured by the area under the ROC curve. Table 4 shows the calculation of the area under the curve for the present example.

TABLE 3

Determination of Specificity and Sensitivity

| Positive if≤ [a] | Sensitivity | 1 - specificity |
|---|---|---|
| 19.86 | .000 | .000 |
| 24.87 | .143 | .000 |
| 29.48 | .286 | .000 |
| 30.54 | .429 | .000 |
| 32.235 | .429 | .143 |
| 33.77 | .571 | .143 |
| 35.11 | .714 | .143 |
| 36.255 | .857 | .143 |
| 37.415 | .857 | .286 |
| 39.23 | .857 | .429 |
| 39.995 | 1.000 | .429 |
| 40.21 | 1.000 | .857 |
| 41.42 | 1.000 | 1.000 |

[a] the smallest cutoff value is the minimum observed test value minus 1 and the largest cutoff value is the maximum observed test value plus 1. All the other cutoff values are the averages of two consecutive ordered observed test values.

TABLE 4

Results Showing Area Under the ROC Curve

| Area | Std. Error [a] | Asymptotic Sig. [b] | Asymptotic 95% Confidence Interval | |
|---|---|---|---|---|
| | | | Lower bound | Upper bound |
| .878 | .096 | .018 | .689 | 1.066 |

Notes:
[a] under the non-parametric assumption
[b] null hypothesis: true area = 0.5

Example 2

Association of Breast Cancer with 4 kb Deletion in Human mtDNA

Twenty breast tissue samples were collected, ten of which were malignant and ten of which had benign breast disease or no abnormalities. These samples were formalin-fixed paraffin embedded and 20 micron sections of each were cut into individual sample tubes for extraction according to the manufacturer's protocol for the QiaAMP DNA Mini Kit (Qiagen P/N 51304). DNA was then quantified using a Nanodrop ND-1000 and normalized to a concentration of 2 ng/ul.

Figure 3:
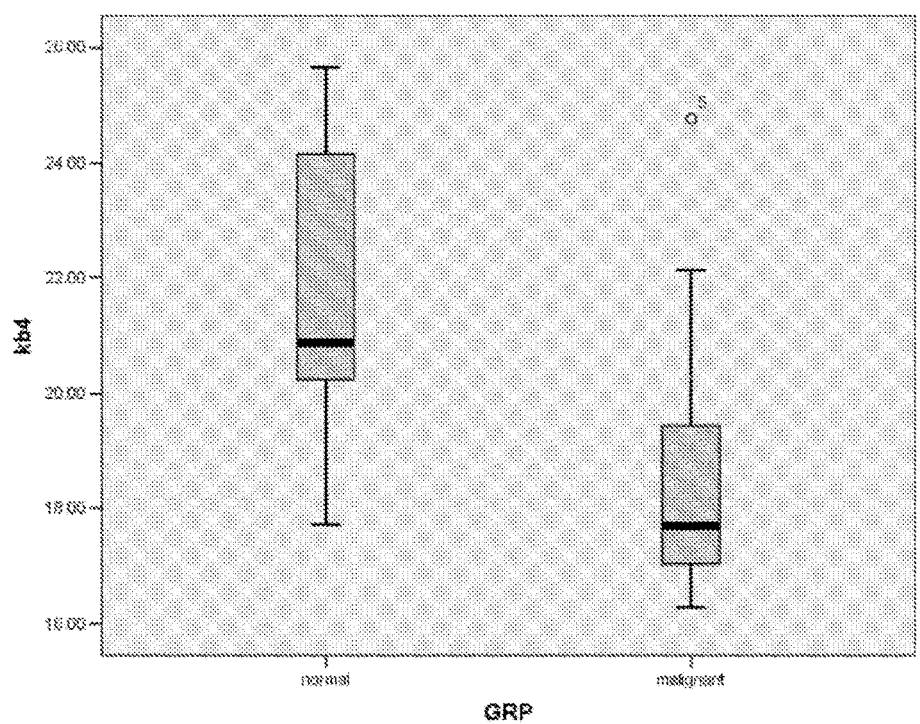
FIG. 3 is a graph showing cycle threshold as related to Example 2.

Samples were then assayed for the levels of the 4 kb deletion by quantitative real-time PCR using the following protocol:
X iQ SYBR Green Supermix (Bio-Rad product no. 170-8880)
175 nmol forward primer (5'-TTGGTGCAACTC-CAAAGCCACCCCTCACC-3') (SEQ ID NO: 4)
175 nmol reverse primer (5'-AGGATGGTGGT-CAAGGGAC-3') (SEQ ID NO: 5)
20 ng template DNA in a 25 ul reaction Reactions were cycled on an Opticon 2 DNA Engine (Bio-Rad Canada) according to the following protocol:
1. 95° C. for 3 minutes
2. 95° C. for 30 seconds
3. 70° C. for 30 seconds
4. 72° C. for 30 seconds
5. Plate Read
6. Repeat steps 2-5 44 times
7. 72° C. for 10 minutes
8. Melting Curve from 50° C. to 105° C., read every 1° C., hold for 3 seconds
9. 10° C. Hold Tables 5 and 6, and FIG. 3 show the difference in the mean $C_T$ scores for breast tissue samples from subjects having malignant breast tissue and benign breast tissue at the 0.065 level.

TABLE 5

Mean Values for $C_T$ scores: Breast Tissue Samples

| Group | N | Mean | Std. Dev. | Std. Error Mean |
|---|---|---|---|---|
| Normal | 9 | 21.5278 | 2.71939 | .90646 |
| Malignant | 9 | 18.9089 | 2.89126 | .96375 |

TABLE 6

Significance Test for Mean $C_T$ scores

| | Levene's Test for Equality of Variances | | Test for Equality Means | | | | | | |
|---|---|---|---|---|---|---|---|---|---|
| CTt40 fluid | F | Sig. | t | df | Sig. (2-tailed) | Mean Diff. | Std. Error Diff. | 95% Confidence Interval of the Difference | |
| | | | | | | | | Lower | Upper |
| Equal variances assumed | .007 | .934 | 1.979 | 16 | .065 | 2.61889 | 1.32306 | −.18588 | 5.42366 |
| Equal variances not assumed | | | 1.979 | 15.94 | .065 | 2.61889 | 1.32306 | −.18674 | 5.42452 |

Figure 4:
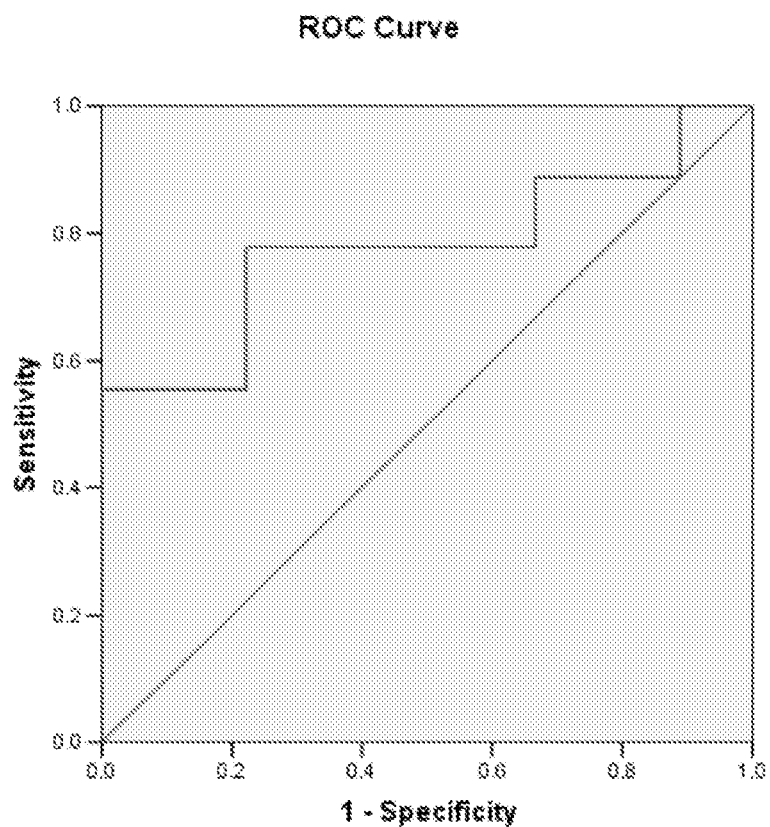
FIG. 4 shows a ROC curve illustrating the specificity and sensitivity of another embodiment of the present invention.

Tables 7 and 8, and FIG. 4 illustrate that when using a cut-off cycle threshold of 19.845 the sensitivity of the assay for breast cancer is 78% and the specificity is 78%.

FIG. 4 is an ROC curve illustrating the specificity and sensitivity of the 4 kb mtDNA deletion as a marker for breast cancer when testing breast tissue. These results were obtained using a cutoff $C_T$ of 19.845. The sensitivity of the marker at this $C_T$ is 78%, while the specificity is 78%.

The determination of the cutoff $C_T$ of 19.845 is shown in Table 7. The results listed in Table 7 show that a cutoff $C_T$ of 19.845 provided the highest sensitivity and specificity.

The accuracy of the test depends on how well the test separates the group being tested into those with and without the breast cancer. Accuracy is measured by the area under the ROC curve. Table 8 shows the calculation of the area under the curve for the present example.

TABLE 7

Determination of Specificity and Sensitivity

| Positive if≤ [a] | Sensitivity | 1 - specificity |
|---|---|---|
| 15.28 | .000 | .000 |
| 16.305 | .111 | .000 |
| 16.69 | .222 | .000 |
| 17.075 | .333 | .000 |
| 17.4 | .444 | .000 |
| 17.71 | .556 | .000 |
| 18.0 | .556 | .111 |
| 18.835 | .556 | .222 |
| 19.415 | .667 | .222 |
| 19.845 | .778 | .222 |
| 20.475 | .778 | .333 |
| 10.79 | .778 | .444 |
| 21.38 | .778 | .556 |

TABLE 7-continued

Determination of Specificity and Sensitivity

| Positive if≤ [a] | Sensitivity | 1 - specificity |
|---|---|---|
| 22.005 | .778 | .667 |
| 23.145 | .889 | .667 |
| 24.19 | .889 | .778 |
| 24.49 | .889 | .889 |
| 25.21 | 1.00 | .889 |
| 26.66 | 1.00 | 1.00 |

[a] the smallest cutoff value is the minimum observed test value minus 1 and the largest cutoff value is the maximum observed test value plus 1. All the other cutoff values are the averages of two consecutive ordered observed test values.

TABLE 8

Results Showing Area Under the ROC Curve

| Area | Std. Error [a] | Asymptotic Sig. [b] | Asymptotic 95% Confidence Interval | |
|---|---|---|---|---|
| | | | Lower bound | Upper bound |
| .778 | .117 | .047 | .548 | 1.008 |

Example 3

Association of Prostate Cancer with 4 kb Deletion in Human mtDNA Using Needle Biopsy Samples Prostate needle biopsy specimens were obtained from 19 individuals, 9 without prostate cancer and 10 with prostate cancer. Needle biopsy tissues were formalin-fixed paraffin embedded (FFPE) as is standard in the clinical diagnostic setting. 10 micron sections of each biopsy were deposited directly into centrifuge tubes and the DNA was extracted using the QiaAMP DNA Mini Kit (Qiagen, p/n 51306). DNA extracts were quantified by absorbance at 260 nm using a NanoDrop ND-1000 Spectrophotometer. Yields ranged from 347 ng to 750 ng. These samples were diluted to 2 ng/ul and amplification reactions setup according to Table 9 and the following:

TABLE 9

Reagents and Concentrations for Amplification Reaction

| Reagent | Final Concentration |
|---|---|
| iQ SYBR Green Supermix (Bio-Rad Laboratories, p/n 170-8882) | 1X |
| Forward Primer 12303-12303/16243-16259F 5'-CCCAAAAATTTTGGTGCAACTCCAAAGCCAC-3' (SEQ ID NO: 6) | 175 nmol |
| Reverse Primer 16410R 5'-AGGATGGTGGTCAAGGGAC-3' (SEQ ID NO: 5) | 175 nmol |
| DNA extract | 0.8 ng/ul |

Nuclease-free water was added to a final reaction volume of 25 ul. Amplifications were carried out on a DNA Engine Chromo4 Real Time PCR Instrument (Bio-Rad Laboratories) according the following cycling conditions:
1) 95° C. for 3 minutes
2) Followed by 45 cycles of
3) 95° C. for 30 seconds
4) 69° C. for 30 seconds
5) 72° C. for 30 seconds
6) Plate Read Then
7) 72° C. for 10 minutes
8) Melting Curve 50° C.-105° C. reading every 1° C., hold for 3 seconds
9) 4° C. Hold Results, shown in Table 10, demonstrate that those individuals with prostate cancer have a lower $C_T$ value and therefore higher levels of the 4 kb deletion in prostate tissue than do those without prostate cancer. Patients with prostate cancer have an average $C_T$ value of 30.7 while the patients without prostate cancer have an average $C_T$ value of 36.4. This difference of 5.7 $C_T$ corresponds to nearly 100 fold greater 4 kb deletion levels in the group with prostate malignancy than in the group without.

TABLE 10

Patient Diagnosis and Associated $C_T$ Score

| Patient Number and Diagnosis | C(t) |
|---|---|
| CUG 1301 Malignant | 25.7 |
| CUG 1268 Malignant | 27.7 |
| CUG RN 345 Normal | 28.3 |
| CUG 1272 Malignant | 28.8 |
| CUG 1375 Malignant | 29.1 |
| CUG 1259 Malignant | 29.1 |
| CUG 1381 Malignant | 30.2 |
| CUG RN 82 Normal | 30.5 |
| CUG 1372 Malignant | 30.9 |
| CUG 1085 C T1 Normal | 31.5 |
| CUG 1317 Malignant | 31.7 |
| CUG 1377 F Normal | 33.6 |
| CUG 1365 B Normal | 34.6 |
| CUG 1370 Malignant | 35.9 |
| CUG RN 405 Normal | 37.5 |
| CUG 1366 Malignant | 37.9 |
| CUG RN 701 Normal | 41.7 |
| CUG RN 420 Normal | 45 |
| CUG RN 373 Normal | 45 |

Tables 11 and 12 show the difference in the mean $C_T$ scores for prostate tissue samples from subjects having normal and malignant prostate tissue.

TABLE 11

Mean Values for $C_T$ Score: Prostate Needle Biopsy Tissue

| Group | N | Mean | Std. Dev. | Std. Error Mean |
|---|---|---|---|---|
| Normal | 9 | 36.4111 | 6.25229 | 2.08410 |
| Malignant | 10 | 30.7 | 3.69534 | 1.16857 |

TABLE 12

Significance Test for $C_T$ Scores

| CTt40 fluid | Levene's Test for Equality of Variances | | Test for Equality Means | | | | | | |
|---|---|---|---|---|---|---|---|---|---|
| | F | Sig. | t | df | Sig. (2-tailed) | Mean Diff. | Std. Error Diff. | 95% Confidence Interval of the Difference Lower | Upper |
| Equal variances assumed | 4.426 | .051 | 2.455 | 17 | .025 | 5.71111 | 2.32589 | .80391 | 10.61831 |
| Equal variances not assumed | | | 2.390 | 12.705 | .033 | 5.71111 | 2.38935 | .53701 | 10.88522 |

Figure 6:
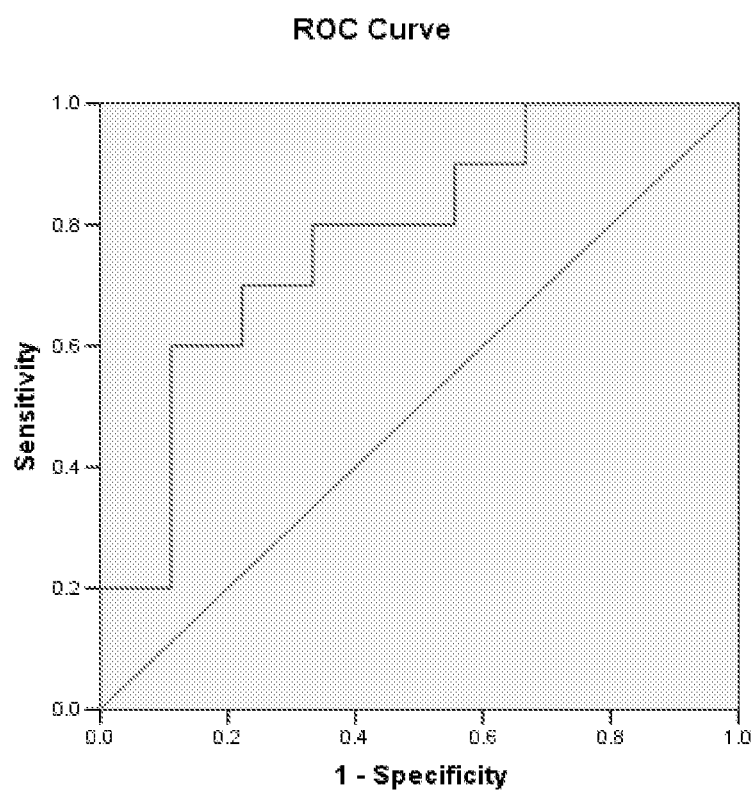
FIG. 6 shows a ROC curve illustrating the specificity and sensitivity of another embodiment of the present invention.

Table 13 and FIG. 6 illustrate that when using a cutoff of $C_T$ 32.65 the sensitivity and specificity of correctly diagnosing these patients is 80% and 67% respectively.

TABLE 13

Determination of Specificity and Sensitivity

| Positive if≤ [a] | Sensitivity | 1 - specificity |
|---|---|---|
| 24.7 | .000 | .000 |
| 26.7 | .100 | .000 |
| 28.0 | .200 | .000 |
| 28.55 | .200 | .111 |
| 28.95 | .300 | .111 |
| 29.65 | .500 | .111 |
| 30.35 | .600 | .111 |
| 30.7 | .600 | .222 |
| 31.2 | .700 | .222 |
| 31.6 | .700 | .333 |
| 32.65 | .800 | .333 |
| 34.1 | .800 | .444 |
| 32.25 | .800 | .556 |
| 36.7 | .900 | .556 |
| 37.7 | .900 | .667 |
| 39.8 | 1.000 | .667 |
| 43.35 | 1.000 | .778 |
| 46.0 | 1.000 | 1.000 |

Although the invention has been described with reference to certain specific embodiments, various modifications thereof will be apparent to those skilled in the art without departing from the spirit and scope of the invention as outlined in the claims appended hereto. All such modifications as would be apparent to one skilled in the art are intended to be included within the scope of the following

REFERENCES

Birch-Machin M A, Online Conference Report (Sunburnt DNA), International Congress of Biochemistry and Molecular Biology, New Scientist, 2000(a).

Birch-Machin M A, Taylor R W, Cochran B, Ackrell BAC, Turnbull D M. *Ann Neurol* 48: 330-335, 2000(b).

Birch-Machin, M. A. (2000). Mitochondria and skin disease. *Clin Exp Dermatol,* 25, 141-6.

Brown, M. D., et al., Am J. Humn Genet, 60: 381-387, 1997.

Bogliolo, M, et al., Mutagenesis, 14: 77-82, 1999.

Chinnery P F and Turnbull D M., Lancet 354 (supplement 1): 17-21, 1999.

Huoponen, Kirsi, *Leber hereditary optic neuropathy: clinical and molecular genetic findings*, Neurogenetics (2001) 3: 119-125.

Hayward S W, Grossfeld G D, Tlsty T D, Cunha G R., *Int J Oncol* 13:35-47, 1998.

Huang G M, Ng W L, Farkas J, He L, Liang H A, Gordon D, Hood R., *Genomics* 59(2):178-86, 1999.

Konishi N, Cho M, Yamamoto K, Hiasa Y. *Pathol. Int.* 47:735-747, 1997.

Landis S H, Murray T, Bolden S, Wngo P A. Cancer *J. Clin.* 49:8-31.

Lee H C, Lu C Y, Fahn H J, Wei YHu. *Federation of European Biochemical Societies,* 441:292-296, 1998.

Naviaux, R K., Mitochondrial Disease—Primary Care Physican's Guide. Psy-Ed. Corp D/B/A *Exceptional Parents Guide:* 3-10, 1997.

Parrella P, Xiao Y, Fliss M, Sanchez-Cespedes M, Mazzarelli P, Rinaldi M, Nicol T, Gabrielson E, Cuomo C, Cohen D, Pandit S, Spencer M, Rabitti C, Fazio V M, Sidransky D: Detection of mitochondrial DNA mutations in primary breast cancer and fine-needle aspirates. Cancer Res 2001, 61:7623-7626.

Polyak Y, et al., *Nature Genet.* 20 (3):291-293, 1998.

Seidman, M. D. et al., *Arch. Otolaryngol Head Neck Surg.,* 123: 1039-1045, 1997.

Sherrat E J, Thomas A W, Alcolado J C., *Clin. Sci.* 92:225-235, 1997.

Shoffner J M, Brown M D, Torroni A, Lott M T, Cabell M F, Mirra S S, Beal M F, Yang C, Gearing M, Salvo R, Watts R L, Juncos J L, Hansen L A, Crain B J, Fayad M, Reckford C L, and Wallace D C., *Genomics* 17: 171-184, 1993.

SpringNet-CE Connection: Screening, Diagnosis: Improving Primary Care Outcomes. Website: http://www.springnet.com/ce/j803a.htm.

Taniike, M. et al., BioChem BioPhys Res Comun, 186: 47-53, 1992.

Valnot, Isabelle, et al., A mitochondrial cytochrome b mutation but no mutations of nuclearly encoded subunits in ubiquinol cytochrome c reductase (complex III) deficiency, Human Genetics (1999) 104: 460-466.

von Wurmb, N, Oehmichen, M, Meissner, C., *Mutat Res.* 422:247-254, 1998.

Wallace et al., Mitochondiral DNA MUtatio Assoicated with Leber's Hereditary Optic Neuropathy, *Science,* 1427-1429.

Wei Y H. Proceedings of the Nat. Sci. Council of the Republic of China April 22(2):5567, 1998.

Woodwell D A. National Ambulatory Medical Care Survey: 1997 Summary. Advance data from vital and health statistics; no. 305. Hyattsville, Md.: National Center for Health Statistics. 1999.

Yeh, J. J., et al., *Oncogene Journal,* 19: 2060-2066, 2000.

Zhang et al., Multiple mitochondiral DNA deletions in an elderly human individual, *FEBS Lett,* 297, 34-38 1992.

Zhang, C., et al., *BioChem. BioPhys. Res. Comun.,* 195: 1104-1110, 1993.

We claim:

1. A method of detecting breast or prostate cancer, or a genetic predisposition to breast or prostate cancer, in a human subject, the cancer being characterized by an elevated amount of mitochondrial DNA (mtDNA) having a deletion of 3926 base pairs within a region of mtDNA between nucleotides 12317 and 16254, with respect to SEQ ID NO. 3, of the human mtDNA genome, the method comprising:
   a) contacting mtDNA extracted from a biological sample from the subject with a pair of PCR primers that specifically bind to a sequence of mtDNA having a spliced region after removal of the deletion, wherein: (i) one of the pair of primers has the nucleotide sequence as set forth in SEQ ID NO: 4; or (ii) the pair of primers have the nucleotide sequences as set forth in SEQ ID NO: 5 and SEQ ID NO: 6, respectively;
   b) quantifying the amount of mtDNA having the deletion by quantifying the amount of mtDNA bound to the primers; and,
   c) detecting said cancer or said predisposition to cancer where the quantified amount of mtDNA having the deletion is elevated in relation to at least one known reference value.

2. The method of claim 1, wherein the pair of primers have the nucleotide sequences as set forth in SEQ ID NO: 4 and SEQ ID NO: 5.

3. The method of claim 1, wherein the primers are amplification primers.

4. The method of claim 3, wherein the step (b) comprises amplifying the region of mtDNA bound to the primer.

5. The method of claim 4, wherein step (b) is conducted using real-time PCR.

6. The method of claim 1, wherein the deletion has the nucleotide sequence as set forth in SEQ ID NO: 1 or SEQ ID NO: 2.

7. The method of claim 1, wherein the at least one known reference value is the amount of mtDNA having the deletion in a reference sample of mtDNA from known non-cancerous tissue or body fluid.

8. The method of claim 7, wherein the biological sample is a tissue or bodily fluid containing cellular material from breast or prostate tissue.

9. A method of detecting breast or prostate cancer, or a genetic predisposition to breast or prostate cancer, in a human subject, the cancer being characterized by an elevated amount of mitochondrial DNA (mtDNA) having a deletion in the human mtDNA genome, the deletion having the nucleotide sequence as set forth in SEQ ID NO: 1 or SEQ ID NO: 2, the method comprising:
   a) contacting mtDNA extracted from a biological sample from the subject with a pair of PCR primers that specifically bind to: i) a sequence of mtDNA having a spliced region after removal of the deletion; or ii) to a sequence of mtDNA comprising the rejoining site of the deletion sequence of SEQ ID NO: 1 or SEQ ID NO: 2 after the deletion sequence has re-circularized, wherein: (i) one of the pair of primers has the nucleotide sequence as set forth in SEQ ID NO: 4; or (ii) the pair of primers have the nucleotide sequences as set forth in SEQ ID NO: 5 and SEQ ID NO: 6, respectively;
   b) quantifying the amount of mtDNA having the deletion by quantifying the amount of mtDNA bound to the primers; and,
   c) detecting said cancer or said predisposition to cancer where the quantified amount of mtDNA having the deletion is elevated in relation to at least one known reference value.

10. The method of claim 9, wherein the pair of primers have the nucleotide sequences as set forth in SEQ ID NO: 4 and SEQ ID NO: 5.

11. The method of claim 9, wherein the primers are amplification primers.

12. The method of claim 11, wherein the step (b) comprises amplifying the region of mtDNA bound to the primer.

13. The method of claim 12, wherein step (b) is conducted using real-time PCR.

14. The method of claim 9, wherein the at least one known reference value is the amount of mtDNA having the deletion in a reference sample of mtDNA from known non-cancerous tissue or body fluid.

15. The method of claim 14, wherein the biological sample is a tissue or bodily fluid containing cellular material from breast or prostate tissue.

16. A method of quantifying, in a biological sample from a human subject, the amount of mitochondrial DNA (mtDNA) having a deletion of 3926 base pairs within a region of mtDNA between nucleotides 12317 and 16254 of SEQ ID NO: 3 corresponding to the human mtDNA genome, the method comprising:
   a) contacting the biological sample with a pair of PCR primers; and,
   b) amplifying and quantifying the amount of mtDNA having the deletion using real-time PCR.

17. The method of claim 16, wherein one primer of the pair of primers has the nucleotide sequence as set forth in SEQ ID NO: 4.

18. The method of claim 17, wherein the other primer of the pair of primers has the nucleotide sequence as set forth in SEQ ID NO: 5.

19. The method of claim 16, wherein the primers have the nucleotide sequences as set forth in SEQ ID NO: 5 and SEQ ID NO: 6.

20. The method of claim 16, wherein the deletion has the nucleotide sequence as set forth in SEQ ID NO: 1 or SEQ ID NO: 2.

21. The method of claim 16, wherein the biological sample is a tissue or bodily fluid containing cellular material from breast or prostate tissue.

* * * * *